United States Patent
Gevaert et al.

(10) Patent No.: US 10,466,232 B2
(45) Date of Patent: *Nov. 5, 2019

(54) CO-CULTURE BIOREACTOR SYSTEM

(71) Applicant: KIYATEC INC., Greenville, SC (US)

(72) Inventors: Matthew R. Gevaert, Greenville, SC (US); David E. Orr, Piedmont, SC (US)

(73) Assignee: KIYATEC INC., Greenville, SC (US)

(*) Notice: Subject to any disclaimer, the term of this patent is extended or adjusted under 35 U.S.C. 154(b) by 372 days.

This patent is subject to a terminal disclaimer.

(21) Appl. No.: 15/406,396

(22) Filed: Jan. 13, 2017

(65) Prior Publication Data

US 2017/0205397 A1    Jul. 20, 2017

Related U.S. Application Data

(63) Continuation of application No. 13/379,152, filed as application No. PCT/US2010/039119 on Jun. 18, 2010, now Pat. No. 9,575,055.

(60) Provisional application No. 61/218,097, filed on Jun. 18, 2009.

(51) Int. Cl.

| C12M 3/00 | (2006.01) |
| C12M 1/00 | (2006.01) |
| G01N 33/50 | (2006.01) |
| C12M 1/42 | (2006.01) |
| C12N 5/09 | (2010.01) |

(52) U.S. Cl.
CPC ......... *G01N 33/5029* (2013.01); *C12M 23/34* (2013.01); *C12M 23/44* (2013.01); *C12M 29/04* (2013.01); *C12M 35/08* (2013.01); *C12N 5/0693* (2013.01); *G01N 33/5011* (2013.01); *G01N 33/5091* (2013.01); *C12N 2500/00* (2013.01); *C12N 2502/00* (2013.01); *C12N 2503/00* (2013.01); *C12N 2503/02* (2013.01)

(58) Field of Classification Search
CPC ...... C12M 23/44; C12M 23/24; C12M 25/02; C12M 29/10
See application file for complete search history.

(56) References Cited

U.S. PATENT DOCUMENTS

| 5,190,878 A | 3/1993 | Wilhelm |
| 5,583,037 A | 12/1996 | Mussi et al. |
| 5,763,275 A | 6/1998 | Nagels |
| 6,451,304 B1 | 9/2002 | Friedmann et al. |
| 8,841,438 B2 | 9/2014 | Tenenbaum et al. |
| 2005/0101010 A1 | 5/2005 | Li |
| 2005/0183334 A1 | 8/2005 | Waters et al. |
| 2006/0199260 A1 | 9/2006 | Zhang et al. |
| 2007/0042490 A1 | 2/2007 | Welter |

(Continued)

FOREIGN PATENT DOCUMENTS

| WO | 2006105329 A2 | 10/2006 |
| WO | 2007021919 A1 | 2/2007 |

(Continued)

OTHER PUBLICATIONS

European Extended Search Report for European Patent Application No. 17200436.8, dated Feb. 27, 2018, 11.

(Continued)

*Primary Examiner* — Nathan A Bowers
(74) *Attorney, Agent, or Firm* — F. Brent Nix, Esq.; Johnson, Marcou & Isaacs, LLC

(57) ABSTRACT

Disclosed herein are bioreactor systems and methods of utilizing said systems.

23 Claims, 19 Drawing Sheets

(56) References Cited

U.S. PATENT DOCUMENTS

| | | |
|---|---|---|
| 2008/0293135 A1 | 11/2008 | Orr et al. |
| 2009/0215176 A1 | 8/2009 | Orr |
| 2011/0027267 A1 | 2/2011 | Kyneb et al. |

FOREIGN PATENT DOCUMENTS

| | | |
|---|---|---|
| WO | WO2009157627 A1 | 12/2009 |
| WO | WO2010040699 A1 | 4/2010 |
| WO | 2010059689 A2 | 5/2010 |
| WO | 2010083532 A1 | 7/2010 |
| WO | 2011094617 A2 | 8/2011 |
| WO | 2013068847 A2 | 5/2013 |

OTHER PUBLICATIONS

European Office Action for counterpart European Patent Application No. 10790240.5, dated Oct. 13, 2015.
Office Action for U.S. Appl. No. 13/379,152, dated Dec. 17, 2015, 12.
Office Action for U.S. Appl. No. 13/379,152, dated Jun. 28, 2016, 11.
Final Office Action for U.S. Appl. No. 13/379,152, dated Sep. 4, 2015, 10.
Dai, et al., "A Co-Cultured Skin Model Based on Cell Support Membranes", Biochemical and Biophysical Research Communications, vol. 329, No. 3, Apr. 15, 2005, 905-908.
Non-Final Office Action for U.S. Appl. No. 13/379,152, dated Jan. 30, 2015, 10.
European Office Action for counterpart European Patent Application No. 10790240.5, dated Feb. 20, 2015, 4.
Supplementary European Search Report for counterpart European Patent Application No. 10790240.5, dated Nov. 15, 2012, 7.
Office Action for U.S. Appl. No. 13/379,152, dated Jul. 31, 2014, 9.
International Search Report and Written Opinion for counterpart PCT Patent Application No. PCT/US2010/039119, dated Mar. 29, 2011, 9.

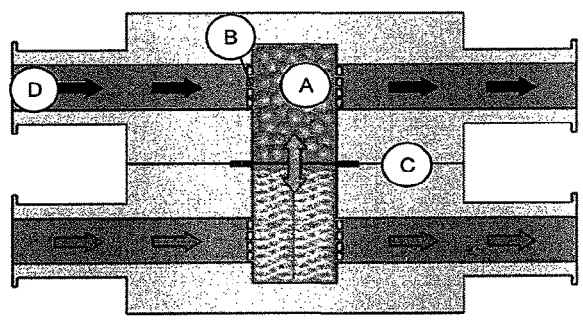
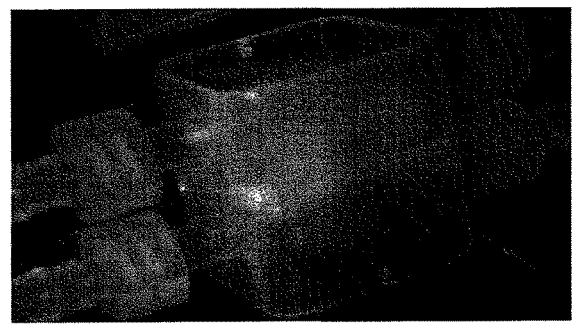
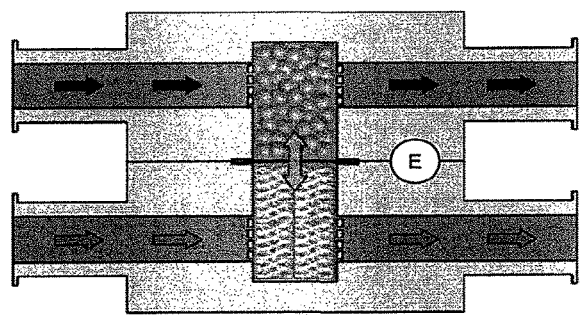
FIG. 18

A.
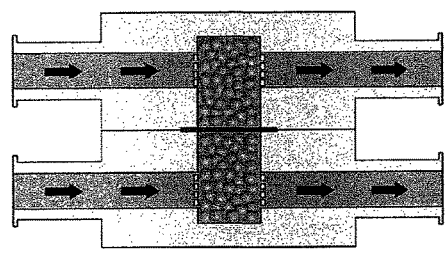
B.
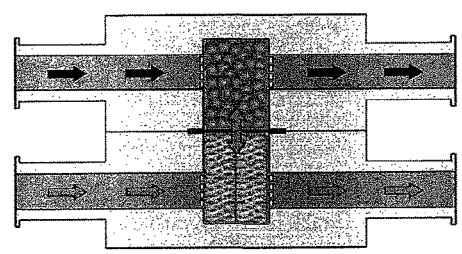
FIG. 20

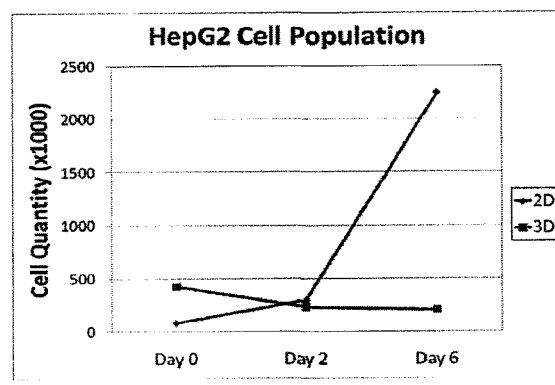
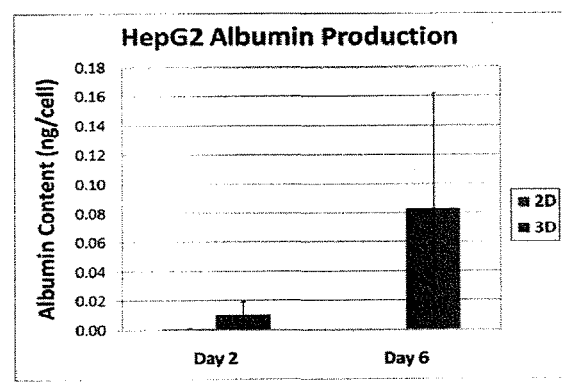
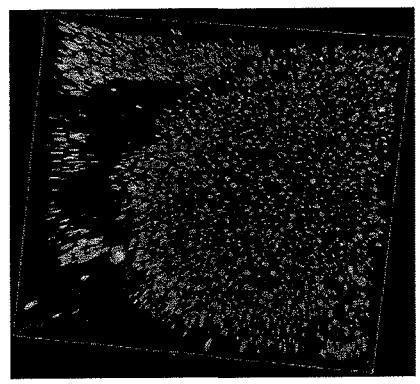
FIG. 21

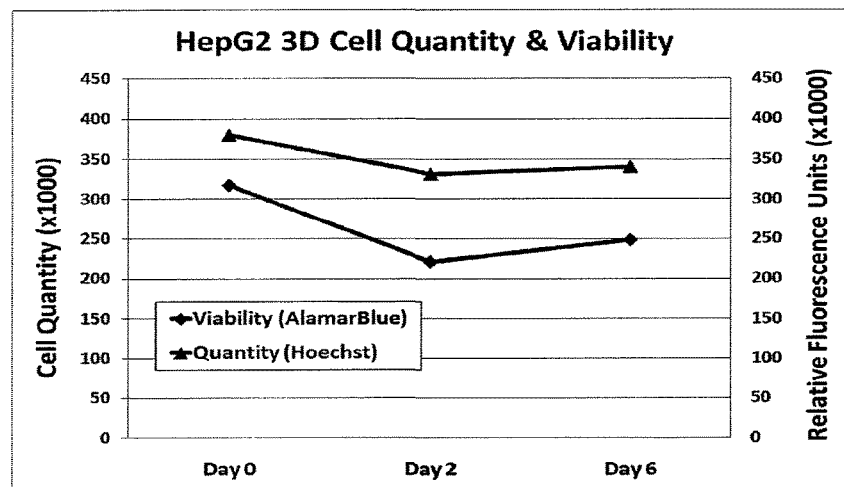
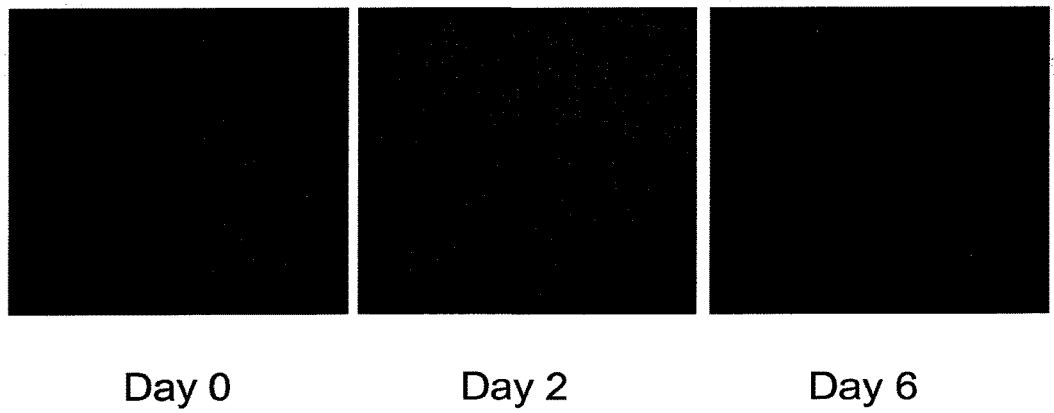
Day 0  Day 2  Day 6
FIG. 22

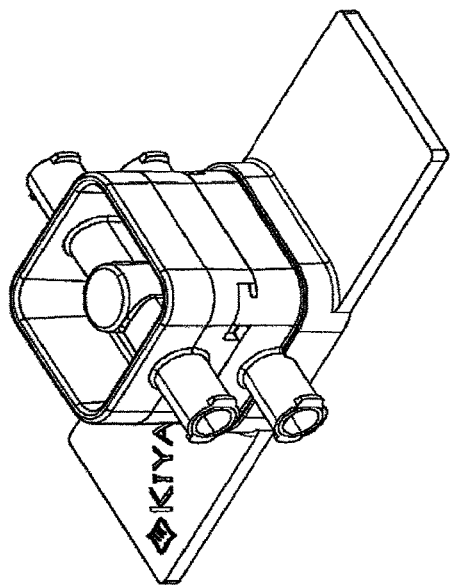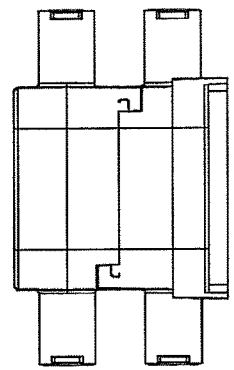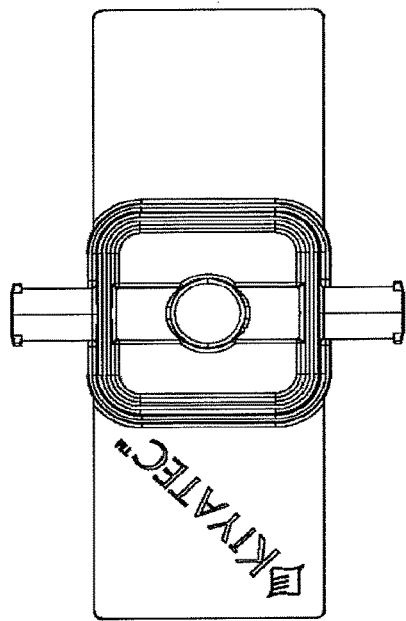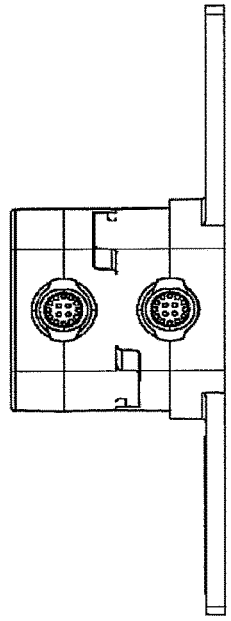
FIG. 23

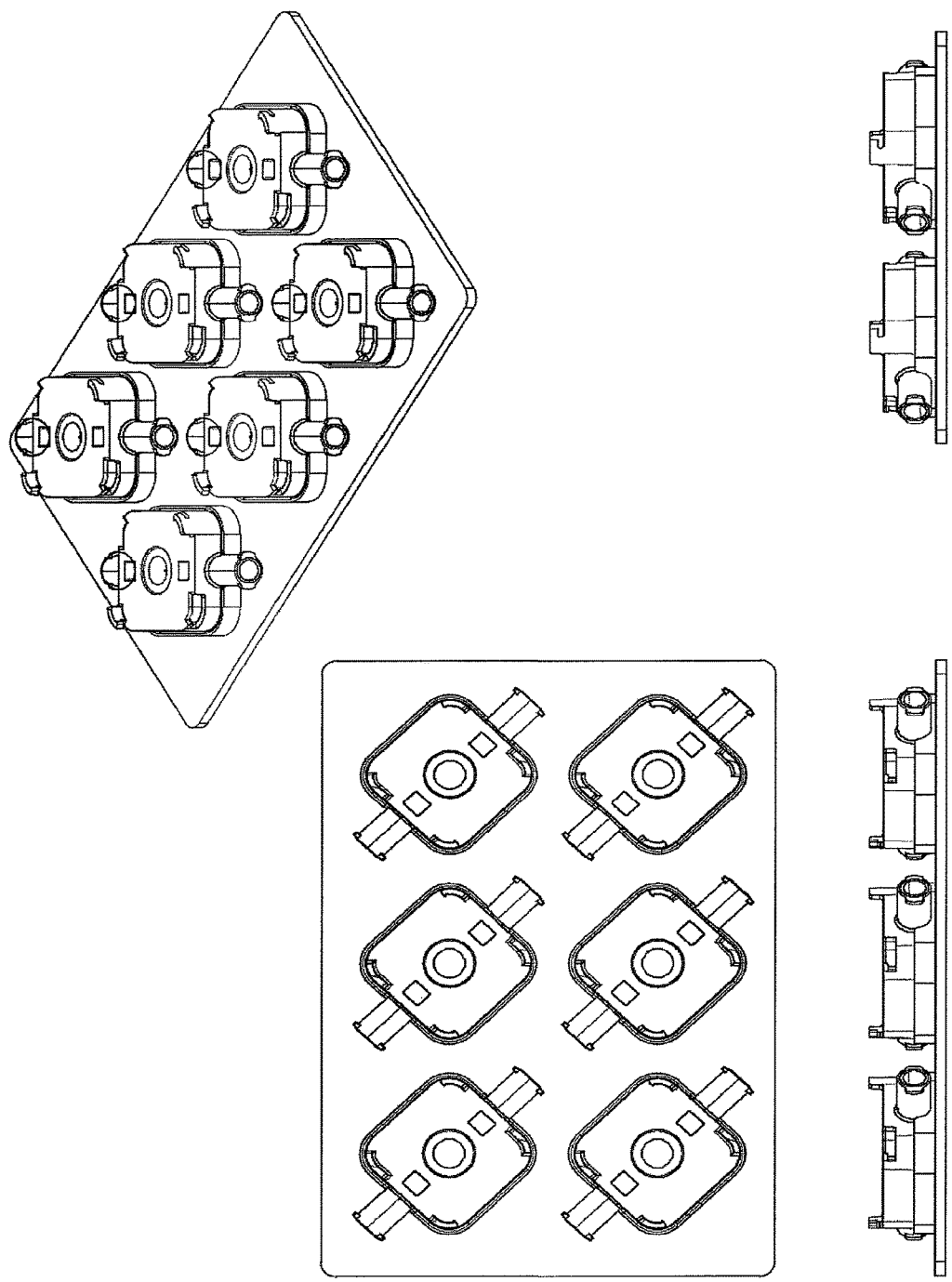

ated Mar. 21, 2012, which is the
CO-CULTURE BIOREACTOR SYSTEM

CROSS REFERENCE TO RELATED APPLICATIONS

This application is a continuation of U.S. patent application Ser. No. 13/379,152, filed Mar. 21, 2012, which is the National Stage of International Application No. PCT/US2010/039119, filed Jun. 18, 2010, which claims the benefit of U.S. Provisional Application No. 61/218,097, filed Jun. 18, 2009. The entire contents of the above-identified priority applications are hereby fully incorporated herein by reference.

BACKGROUND OF THE INVENTION

The ability to culture in vitro viable three-dimensional cellular constructs that mimic natural tissue has proven very challenging. One of the most difficult of the many problems faced by researchers is that there are multiple dynamic biochemical interactions that take place between and among cells in vivo, many of which have yet to be fully understood, and yet the complicated in vivo system must be accurately modeled if successful development of engineered tissues in vitro is to be accomplished. The ideal in vitro system should accurately model the mechanical environment as well as the essential cellular interactions found during in vivo development while providing purity of the desired product construct so as to enable utilization of the product, for instance as transplantable tissue. For example, it is commonly desired that the product cells be isolated and free from extraneous cells of other phenotypes, and in particular those previously shown to exhibit unfavorable attributes following implant (e.g., tumor generation or immune system reaction). However, biochemical interaction between those less than desirable cell types with the product cells may be necessary for the healthy growth and development of the product cells, for example due to their introduction of growth stimulation factors into the culture environment.

Many existing co-culture systems are simple well plate designs that are static in nature and do not allow for manipulation of the local environment beyond the gross chemical inputs to the system. As such, the development of more dynamic co-culture systems has become of interest. However, known dynamic systems, similar to the static systems, often provide only a single source of nutrients/growth stimulants/etc. to all of the cell types held in the system.

Moreover, the different cell types that are co-cultured in both static and dynamic systems are usually maintained in actual physical contact with one another, preventing the development of an isolated cell population, and also limiting means for better understanding the biochemical communications between the cell types during growth and development.

There are some systems in which an attempt has been made to physically separate cell types in dynamic systems, for instance through location of a porous substrate between the two cell types. However, in these systems, all cell-types cultured in the system are still subjected to the same culture media, similar to the above-described static systems. Additionally, the porous substrate usually also serves as the support scaffold to which cells are intended to attach and grow. Attachment of cells to the porous substrate will alter the flow characteristics of biochemicals across and through the substrate, which in turn affects communication between the cells.

What is needed in the art is a method for co-culturing multiple cell types in a dynamic environment in which the different cell types can communicate biochemically, and yet can be separated physically. Moreover, what is needed is a system in which cells can be developed to form a three-dimensional construct, while maintaining the isolation and purity of the developing product cells and at the same time allowing for biochemical communication between cells of different types.

SUMMARY

In one aspect, the present invention is directed to a bioreactor system. The disclosed bioreactor system can comprise a single or a multiple culture system, such as a co-culture system. Thus, in another aspect, the present invention is directed to a bioreactor system that can maintain different cell types in physically isolated environments without soluble factor exchange. In yet another aspect, the present invention is directed to a bioreactor system wherein the bioreactor system is a co-culture bioreactor system that can maintain different cell types in physically isolated environments but can allow biochemical communication between the different cell types. In one aspect, a bioreactor system of the invention can comprise at least one culture chamber defining an inlet, an outlet, and a port that are in communication with an interior volume of the at least one culture chamber. In one non-limiting example, the at least one culture chamber comprises a first culture chamber and a second culture chamber. In this aspect, the first culture chamber defines a first inlet and a first outlet that is configured to allow fluid to selectively flow through the interior of the first culture chamber. In a further aspect, the first culture chamber defines a first port that is in communication with the interior of the first culture chamber. The second culture chamber defines a second inlet and a second outlet that is configured to allow a second fluid to selectively flow through the interior of the second culture chamber. In a further aspect, the second culture chamber defines a second port that is in communication with the interior of the second culture chamber.

In another aspect, the system can also comprise a membrane, which can be positioned, for example and without limitation, between the respective ports of adjoining first and second culture chambers. The membrane can be semi-permeable and can have a porosity that is configured to allow passage of cellular expression products through the membrane, but prevent passage of the cells, which are disposed therein either chamber, through the membrane. In one embodiment, the membrane can be formed of a material, for example and without limitation a polycarbonate, which can discourage cellular attachment to the membrane.

In a further aspect, the bioreactor systems of the invention can comprise a cellular anchorage in one or both of the respective culture chambers. Suitable cellular anchorage can be formed of multiple discrete scaffolds or single continuous scaffolds. Multiple discrete scaffolds can be maintained within a culture chamber through utilization of a retaining mesh that can hold the scaffolding materials within the chamber and prevent the loss of the scaffolding materials through the outlet of the culture chamber.

In one aspect, a cellular anchorage can be maintained at a predetermined distance from the membrane that separates the chambers. In one aspect, this predetermined distance can be selected to effect prevention or minimization of attachment of cells to the membrane and can act to maintain the physical isolation of different cell types within their respective culture chambers.

The bioreactor system can also be capable of incorporating additional culture chambers that can be in biochemical communication with one or both of the other two culture chambers. For instance, the at least one chamber can further comprise a third chamber that can be configured to selectively house cells that can be selectively positioned in biochemical communication with the one or more of the system culture chambers, optionally with a membrane separating the first and third chambers, though this aspect is not a requirement of the system.

It is contemplated that, in operation, the bioreactors and the cells disposed therein can optionally be subjected to at least one mechanical stimuli. For example and without limitation, pressurized fluid perfusion through a culture chamber can subject developing cells to shear stress; an adjacent pressure module can be utilized to subject the interior of a culture chamber to hydrostatic loading, and the like.

It is also contemplated that the bioreactors of the system can be used for growth and development of isolated cells in various different applications. For instance, three-dimensional cellular constructs can be formed including only the cells that are isolated in one of the culture chambers of the reactor system. In one exemplary aspect, a culture chamber can be seeded with undifferentiated cells, and the method can comprise triggering differentiation of the cells via the biochemical triggers provided from the cells of the second culture chamber.

BRIEF DESCRIPTION OF THE DRAWINGS

The accompanying drawings, which are incorporated in and constitute a part of this specification, illustrate certain aspects of the instant invention and together with the description, serve to explain, without limitation, the principles of the invention. Like reference characters used therein indicate like parts throughout the several drawings.

FIG. 3 is one embodiment of a bioreactor system of the present invention including two adjacent cell modules having independently controlled flow characteristics there through;

FIG. 18 shows cross section and actual image of 30 culture system assemblies.

FIG. 20 shows example assembly of modules for monoculture (A) and co-culture (B).

FIG. 21 shows the difference between 2D and 3D culture systems utilizing the same culture conditions.

FIG. 22 shows cellular metabolism assays results following 3D culture;

FIG. 23 shows a first and second cell module engaged through the use of male fittings and female fittings. FIG. 23 further shows said cell modules mounted in a microscope stage adapter.

FIG. 24 shows six cell modules mounted to well plate adapter for use in instrumentation, i.e., spectrometer plate reader.

DETAILED DESCRIPTION OF THE INVENTION

Figure 1A:
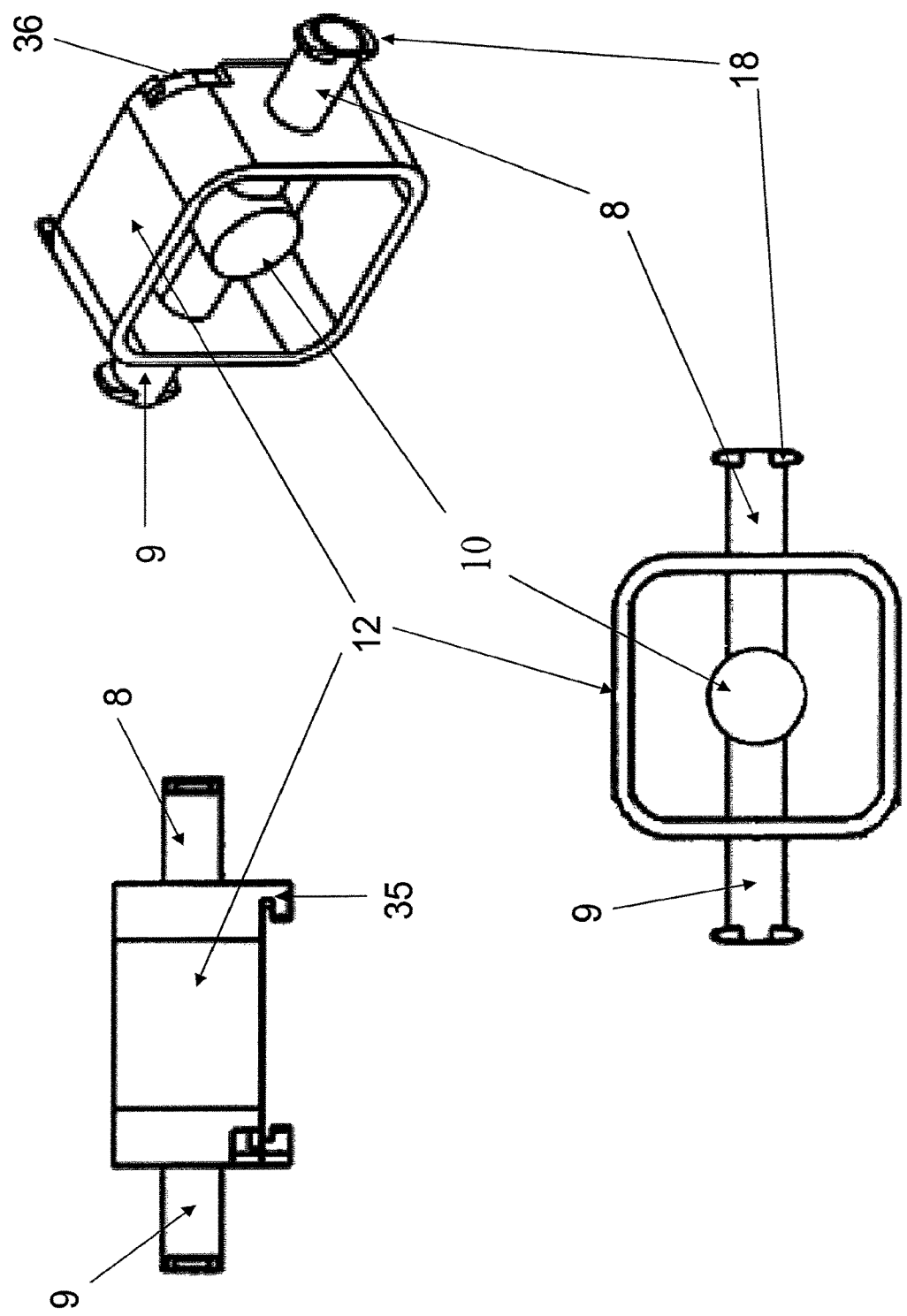
FIG. 1A and FIG. 1B are views of one embodiment of the cell modules of the bioreactor system.

The present invention can be understood more readily by reference to the following detailed description, examples, drawings, and claims, and their previous and following description. However, before the present devices, systems, and/or methods are disclosed and described, it is to be understood that this invention is not limited to the specific devices, systems, and/or methods disclosed unless otherwise specified, as such can, of course, vary. It is also to be understood that the terminology used herein is for the purpose of describing particular aspects only and is not intended to be limiting.

The following description of the invention is provided as an enabling teaching of the invention in its best, currently known embodiment. To this end, those skilled in the relevant art will recognize and appreciate that many changes can be made to the various aspects of the invention described herein, while still obtaining the beneficial results of the present invention. It will also be apparent that some of the desired benefits of the present invention can be obtained by selecting some of the features of the present invention without utilizing other features. Accordingly, those who work in the art will recognize that many modifications and adaptations to the present invention are possible and can even be desirable in certain circumstances and are a part of the present invention. Thus, the following description is provided as illustrative of the principles of the present invention and not in limitation thereof.

As used herein, the singular forms "a," "an," and "the" comprise plural referents unless the context clearly dictates otherwise. Thus, for example, reference to a "chamber" comprises aspects having two or more such chamber unless the context clearly indicates otherwise.

Ranges can be expressed herein as from "about" one particular value, and/or to "about" another particular value. When such a range is expressed, another aspect comprises from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

As used herein, the terms "optional" or "optionally" mean that the subsequently described event or circumstance may or may not occur, and that the description comprises instances where said event or circumstance occurs and instances where it does not.

In simplest terms, disclosed herein are bioreactor systems. In one aspect, the bioreactor systems disclosed herein comprise at least one cell module defining a culture chamber, an inlet, an outlet, and at least one port opening. The cell modules of the bioreactor system can be engaged to form multi-chambered bioreactor systems. Thus, in one aspect, disclosed herein are bioreactor systems comprising at least one first cell module defining a first cell culture chamber, an inlet, an outlet, and a port opening, wherein the port opening is on one end of the cell culture chamber and at least one second cell module defining a second cell culture chamber, an inlet, an outlet, and a port opening, wherein the port opening is on one end of the cell culture chamber. It is understood that the first and second culture chambers respectively defining the first and second cell modules can be separated by a barrier such as a membrane. Thus, in another aspect, disclosed herein are bioreactor systems comprising at least one first cell module defining a first cell culture chamber, an inlet, an outlet, and a port opening, wherein the port opening is on one end of the cell culture chamber and at least one second cell module defining a second cell culture chamber, an inlet, an outlet, and a port opening, wherein the port opening is on one end of the cell culture chamber; a membrane positioned between the open port of said first cell module and the open port of said second cell module.

It is further understood that the first and second cell module can be physically engaged. Thus, in still another aspect, disclosed herein are bioreactor systems comprising at least one first cell module defining a first cell culture chamber, an inlet, an outlet, and a port opening, wherein the port opening is on one end of the cell culture chamber and at least one second cell module defining a second cell culture chamber, an inlet, an outlet, and a port opening, wherein the port opening is on one end of the cell culture chamber; a membrane positioned between the open port of said first cell module and the open port of said second cell module; and wherein the first cell module and second cell module are sealingly engaged securing the membrane between the first and second module.

The disclosed bioreactor systems can be assembled to allow for single or multiple cultures of tissues or cells. Thus, in one aspect, the bioreactor system is directed to multi-chambered systems, such as a co-culture bioreactor system, and can, for example, be utilized for the growth and development of isolated cells of one or more cell types in a dynamic in vitro environment more closely resembling that found in vivo. For instance, the multi-chambered bioreactor system can allow biochemical communication between cells of different types while maintaining the different cell types in a physically separated state, and moreover, can do so while allowing the cell types held in any one chamber to grow and develop with a three-dimensional aspect. In addition, the presently disclosed bioreactor system can allow for variation and independent control of environmental factors within the individual chambers. For instance, it is contemplated that the chemical make-up of a nutrient medium that can flow through a chamber as well as the mechanical force environment within the chamber including the perfusion flow, hydrostatic pressure, and the like, can be independently controlled and maintained for each separate culture chamber of the disclosed systems (see, for example, FIGS. 18 and 20).

In still another aspect, disclosed herein are methods of using the bioreactor systems disclosed herein for the growth and maturation of three-dimensional tissue for in vivo implantation. The disclosed methods can comprise culturing of one or more tissues using the disclosed bioreactor systems. The disclosed methods can further comprise single or co-culture applications. Thus, disclosed herein are methods of growing three-dimensional tissue comprising the maturation of a single tissue preferentially stimulated by another cell population through soluble factor exchange across a membrane. Also disclosed herein are methods of growing three-dimensional tissue for use in in vivo implantation comprising the simultaneous maturation of two tissues connected through soluble factor exchange across a membrane 23. In another aspect, the disclosed methods can comprise the simultaneous and independent maturation of two tissues with no soluble factor exchange. It is understood that such a method could be accomplished through the use of a non-permeable membrane.

In one aspect, it is contemplated that the bioreactor systems can be utilized for culturing product cells for medical use, for example and without limitation, for use as a drug-discovery test system for pharmacokinetics (for example, toxicology and Absorption Distribution Metabolism and Elimination (ADME)), for culturing a biopsy for use as a tissue-based diagnostic, for transplant to a patient; or for manufacture of a protein product; such as a biopharmaceutical. Thus, for example disclosed herein are methods of pharmacokinetic screening, comprising a) culturing one or more cells in the cell culture chamber of a first cell module in the bioreactor system disclosed herein; b) passing an agent through the inlet and outlet of the first cell module; and c) detecting the presence of an increase, decrease, or no change in the rate or amount of a pharmacokinetic effect on the one or more cells in the second cell culture chamber; wherein an increase, decrease, or no change in the pharmacokinetic effect relative to a control provides information on the pharmaceutical properties of the agent. Also disclosed are methods of pharmacokinetic screening, comprising a) culturing one or more cells of a first cell type in the cell culture chamber of a first cell module; b) culturing one or more cells of a second cell type in the cell culture chamber of a second cell module; c) passing an agent through the inlet and outlet of the first cell module; wherein the cell culture chamber of the first cell module and the cell culture chamber of the second cell module are separated by a membrane; and d) detecting the presence of an increase, decrease, or no change in the rate or amount of a pharmacokinetic effect on the one or more cells in the second cell culture chamber;

wherein an increase, decrease, or no change in the pharmacokinetic effect relative to a control provides information on that agent's pharmaceutical properties.

According to the pharmacokinetic aspects disclosed herein, cells can be grown in an environment that comprises the biochemical products of different cell types, at least some of which may be necessary for the growth and development of the desired cells. However, it is contemplated that cell types can be maintained in a physically isolated state during their growth and development. As such, possible negative consequences due to the presence of aberrant or undesired cell types in the desired product cells can be avoided.

In another aspect, it is contemplated that the bioreactor systems disclosed herein can be utilized for the replication of biological conditions such as cell migration/invasion such as, for example and without limitation, wound healing, metastasis, vasculogenesis, immune responses, angiogenesis, tumor formation, and chemotaxis. Additionally the bioreactor systems disclosed herein can be utilized for the replication of biological conditions involved in cellular proliferation, cell survival, and attachment. Used in such a manner the bioreactor system provides the extracellular contact and milieu to more closely replicate the intact biological system. In a like manner, the bioreactor systems disclosed herein can be utilized as the framework for cell migration assays. It is contemplated that cell migration/invasion assays can look at the movement of cells across a membrane through the use of a Boyden chamber or in a manner similar to a Boyden chamber utilizing a permeable membrane 23 with a pore size similar or identical to that used in a Boyden chamber. For example, the membrane 23 can have a pore size between 0.2 µm and 10 µm. As contemplated herein, cells are deposited into a first chamber with a permeable membrane separating the cells from a second chamber. Media is placed in a second chamber that encourages migration (such as the presence of or a higher concentration of serum, cytokine, or chemokine). Alternatively, factors such as electric current, pressure, and media flow rate can be utilized to encourage or discourage migration. Migratory cells move across the membrane while non-migratory cells remain in the first chamber. In one example, after the cells have been allowed to migrate, the migratory cells can be disassociated from the membrane utilizing conventional means, such as, without limitation, a suitable detachment buffer. In another example, cell migration does not stop on the opposing side of the membrane 23, but continues to a scaffold in the second chamber.

In another aspect, the bioreactor system disclosed herein can be used for the separation and isolation of cells. That is, the disclosed bioreactor system can be used to separate and isolate cells of one type from a mixed population of cells or tissue. For example, the disclosed bioreactor system can be used for the separation and isolation of stem cells from a mixed population of cells such as bone marrow, or umbilical cord blood.

The use of bioreactor systems as devices for performing cell separation and isolation, cell migration/invasion assays, or replicating bioreactor systems is of significant importance to the study of many diseases and conditions. For example, diseases where excessive angiogenesis has been implicated include, but are not limited to, rheumatoid arthritis, cancer, psoriasis, and diabetic retinopathy. Diseases where insufficient angiogenesis has been implicated include but are not limited to stroke, heart disease, ulcers, infertility, and scleroderma. Accordingly, the bioreactor systems disclosed herein and their use in cell migration/invasion assays have considerable use and commercial significance to the identification of regulatory pathways or migration/invasion and modulators of migration/invasion. Thus, in one aspect, disclosed herein are methods of screening for an agent that modulates cell migration/invasion, comprising culturing one or more cells in the cell culture chamber of a first cell module; passing an agent through the inlet and outlet of a second cell module; wherein the cell culture chamber of the first cell module and the cell culture chamber of the second cell module are separated by a membrane detecting the presence of an increase, decrease, or no change in the rate or amount of cellular migration across the membrane; and wherein an increase or decrease in cellular migration in the presence of the agent relative to a control indicates an agent that modulates cell migration/invasion.

In another application, the bioreactor system can be used to more closely study the biochemical communication between different cell types and the influence of this biochemical communication on the growth and development of cells. As the local environment within each culture chamber of the bioreactor system can be substantially independently controlled while biochemical communication between chambers can be maintained, information regarding the growth and development of cells and the influence of the local environment on that growth and development can be examined through use of the bioreactor system.

In yet another embodiment, undifferentiated stem cells can be located in a first chamber of the bioreactor system, and one or more types of feeder cells can be located in adjacent chamber(s), which, as one skilled in the art will appreciate, can selective be in biological communication with the first chamber. Such a bioreactor system can be utilized to, for example and without limitation, study the triggering mechanisms involved in stem cell differentiation or to provide isolated, differentiated cells for implantation.

Cells and tissues used in the disclosed bioreactor systems and methods can be obtained by any method known to those of skill in the art. Examples of sources of cells and tissues include without limitation purchase from a reliable vendor, blood (including peripheral blood and peripheral blood mononuclear cells), tissue biopsy samples (e.g., spleen, liver, bone marrow, thymus, lung, kidney, brain, salivary glands, skin, lymph nodes, and intestinal tract), and specimens acquired by pulmonary lavage (e.g., bronchoalveolar lavage (BAL)). The source of cells and tissues obtained from blood, biopsy, or other direct ex vivo means can be any subject having tissue or cells with the desired characteristics including subject with abnormal cells or tissues which are characteristic of a disease or condition such as, for example, a cancer patient. Thus, it is contemplated herein that the subject can be a patient. It is also understood that there may be times where one of skill in the art desires normal tissues or cells. Thus, also disclosed herein are tissues and cells obtained from a normal subject wherein a "normal" subject refers to any subject not suffering from a disease or condition that affects the tissues or cells being obtained. It is further understood that the subject can comprise an organism such as a mouse, rat, pig, guinea pig, cat, dog, cow, horse, monkey, chimpanzee or other nonhuman primate, and human.

Therefore, it is contemplated that exemplary cell types comprise, at least partially and without limitation: Primary-hBM SC; Primary-hSkin FB; Primary-cow CC; primary-rat BMSC; Primary-h CC; MC3T3-E1; Primary-hUVEC; Primary-rabbit CC; NIH 3T3; Primary-CC; Primary-rat Liver Hep; Primary-hSkin Keratinocyte; MG63; HEP-G2; L929; Primary-BM SC; Primary-rabbit BM SC; Primary-pig CC;

Primary-hBone OB; MCF-7; Primary-rat Heart CM; Primary-h Foreskin FB; Primary-hAdipose SC; Primary-hFB; #NIA; Primary-hAdipose SC; Primary-PB; Primary-ratAortaSMC; Primary-Bone; Primary-dog CC; 3T3 (nonspecific); C2C12; MDA-MB-231; SaOS-2; Primary-mouse BM SC; Primary-rat CC; Primary-h Mesoderm Mes Pre C; Primary-rat Brain Neuronal; PC12; Primary-Cancerous; Primary-h Skin EC; Primary-rat BM OB; Primary-mouse Embryo SC; MCF-10A; Primary-h Bone OB-like; Primary-goat BMSC; Primary-h Aorta SMC; MDCK (Madin-Darby Canine Kidney); Primary-hl DAnnulus C; Primary-ratBone OB; Primary-h Adipose Preadipocyte; Primary-SC; Primary-rat Skeletal Muscle Myoblast; Primary-Heart CM; Primary-cow AortaEC; Primary-dog BM SC; Primary-sheep BM SC; Primary-sheep CC; Primary-pig BMSC; Primary-cow BMSC; Primary-h BladderSMC; Primary-pig Aorta EC; Primary-h Cornea Epi C; Primary-h Aorta EC; Primary-h Cornea FB; Primary-pig Aorta SMC; Primary-mouse Liver Hep; A549; Primary-Bone OB; Primary-h Bladder Uro; Primary-h UV SMC; Swiss 3T3; Primary-Liver Hep; Primary-h Lig FB; Primary-h Coronary Artery SMC; Primary-OB-like; Primary-h Teeth Mes Pre C; HT1080; Primary-rat Heart FB; Primary-pig HV Intersticial C; C3A; Primary-h Breast Cancerous; Primary-h Foreskin Keratinocyte; Primary-h Oral Mucosa Keratinocyte; Primary-mouse Ovary Oocytes; Primary-h Vase SMC; 3T3-L1; Primary-h Lung FB; Primary-chicken Ganglia Neuronal; Primary-h U CStC; Primary-cow Aorta SMC; Primary-mouse Embryo FB; Primary-h Bronchi EpiC; CHO-K1; Primary-h Liver Hep; Primary-hSaphVEC; Primary-hTeethPDL; Primary-rat Skin FB; Primary-pig Liver Hep; PC-3; Primary-SMC; Primary-hMVEC; Primary-mouseFB; Primary-h Nasal Chondrocyte; Primary-hCorneaKeratinocyte; Primary-hOvaryCancerous; Primary-h U CBSC; Primary-rat Heart EC; Primary-Vase; Primary-mouse Skin FB; Primary-h Tendon TC; Primary-rat Brain Astrocyte; Primary-rat Nerve SC; Ha CaT; Primary-h Gingiva FB; Primary-Neural; Primary-cow Bone OB; Primary-rat Adipose SC; Primary-mouse Bone OB; Primary-h Teeth PC; Primary-h Blood Mononuclear; Primary-rat Hippocampus Neuronal; D3; HeLa; HEK293; Cl 7.2; Primary-h Skin Melanocyte; Primary-h Blood EC-like; HOSTE85; Primary-h UC SC-like; Primary-h Cornea SC; Primary-rat Aorta EC; Primary-h Saph VSMC; Primary h UCBEC; Primary-mouse Heart CM; D1 ORL UVA; Primary-h Coronary Artery EC; Primary-h Aorta Myo FB; HT-29; Primary-h Tendon FB; RAW 264; Primary-rat Dental Pulp SC; 3T3-J2; H1; Primary-pig Teeth; Primary-rat Sciatic Schwann; Primary-rabbit Bone OB-like; Primary-sheep Aorta EC; Primary-rabbit Cornea Epi C; Primary-h Ovary Epi C; Primary-rabbit Ear Chondrocyte; SH-SY5Y; Primary-h Teeth FB; Primary-h Oral Mucosa FB; Primary-rabbit FB; C6; Primary-rat Testes Stertoli; Primary-cow Arterial EC; Primary-pigHVEC; Primary-cow Nucleus Pulposus Cells; Primary-rat Ganglia Neuronal; Primary-dog Bladder SMC; Primary-Vase SMC; 129/SV; Primary-pig Ear Chondrocyte; ED27; Primary-rabbit Bone B; Primary-h Brain Glioblast; Primary-rat Adipose Preadipocyte; Primary-h Cartilage Synov; Primary-rat Pancreas Insulin; Primary-hEC; Primary-sheep Aorta SMC; Primary-h Endometrium EpiC; U251; Primary-h Endometrium StC; Primary-pig Bladder SMC; Primary-h HVIintersticial C; Primary-pig Esoph SMC; Primary-h NP Neuronal; Primary-rabbit Aorta SMC; Primary-h NSC; Primary-rabbit CorneaFB; Primary-h oral Cancerous; Primary-rabbit Lig FB; Primary-h SC; Primary-rat BMOB-like; Primary-h Skeletal Muscle Myoblast; COS-7; C-28/I2; HK-2; Primary-h Uterus Cancerous; Primary-rat Ventricle CM; Primary-h Vasc EC; Primary-sheep Carotid Artery SMC; HCT-116; ROS 17/2.8; Primary-h Vocal FB; UMR-106; Primary-mouse Aorta SMC; H9; RI; Primary-rat Fetal Neuronal; Primary-chicken Ear EpiC; Huh7; Primary-rat Vase SMC; Primary-h NP SC; ES-D3; IMR-90; Primary-rat Bladder SMC; 293T; Primary-h Foreskin VascularEC; Primary-h Placenta EC; Primary-h Lung EpiC; Primary-h Prostate EpiC; U-87 MG; Primary-dog Carotid Artery SMC; Primary-rabbit Cornea StC; Primary-dog ID Annulus Fibrosus; Primary-chicken Embryo Chondrocyte; Primary-EC; HFF; Vero; HFL-1; Primary-h Adipose FB; Primary-cow FB; Primary-h UTSMC; Primary-rat Ventricle FB; AH 927; Primary-sheep Vase FB; DU-145; ST2; Bl6.FI0; Primary-h Nasal EpiC; Primary-ID Annulus C; Primary-h Dental Pulp SC; 3HIOTI/2; Primary-Heart Valve; Primary-h Bone Alveolar; Primary-rabbit Tendon FB; Primary-mouse Kidney Insulin; HEPM; Primary-baboon Aorta SMC; HTK; Primary-mouse MDSC; Primary-rat Esoph EpiC; Primary-mouse Nerve SC; Primary-h Fetus OB-like; Primary-mouse Skeletal Muscle SC; hFOB 1.19; Primary-Nerve Schwann; Primary-h Ganglia Neuronal; Caco-2; Primary-h Kidney Renal; Primary-h Breast EpiC; Primary-h Liver SC; Primary-pig Bladder Uro; Primary-h Lung EC; Primary-h Breast FB; Primary-sheep Jugular Vein EC; Primary-pig Esoph EpiC; Primary-h•Lymph EC; Primary-chicken CC; Primary-h Lymph TCell; Primary-h Colon Adenocarcinoma; Primary-h Mammary EC; Primary-pig Vocal FB; Primary-h Mammary EpiC; Primary-rabbit Adipose SC; Primary-h Cornea EC; H9c2; Primary-h UT StC; Primary-cat Heart CM; Primary-mouse Pancreas EpiC; HS-5; Primary-sheep Skeletal Muscle Fetus Myoblast; Primary-cow ID; Primary-mouse BM OCpre; Primary-cow Knee Meniscus C; Hep-3B; Primary-cow Lig FB; HL-1; HuS-E/2; RWPE1; Primary-cow Retina EpiC; Primary-hVascMyoFB; IEC-6; Primary-mouse Fetal Hep; HS68; OVCAR-3; Primary-dog Knee MeniscusC; Primary-rabbit Mesoderm Mes PreC; Primary-dog Lig FB; Primary-rat Lung Alveolar; Primary-dog Skin Keratinocyte; CRL-11372; Primary-dog Vasc SMC; HMEC-1; Primary-Embryo SC; T-47D1; Primary-goatCC; Primary-h UVSC-like; Primary-guinea pig Ear EpiC; Primary-Ligament; Primary-guinea pig Skin FB; Primary-mouse Cortical Neuronal; Primary-hAdipose Adipocyte; Primary-mouse Liver SC; Primary-h Adipose FB-like; CAL72; J774; P19; Primary-h Amniotic fluid; Primary-rabbit Cornea EC; Primary-h Amniotic FSC; Primary-rat BMFB-like; ARPE-19; Primary-rat Kidney Mesangial; K-562; Primary-rat Nasal Ensheathing; Primary-h Bladder StC; Primary-chicken Embryo Proepicardium; ATDC5; Primary-sheep FB; Kasumi-1; Primary-Skeletal Muscle; Primary-h Bone Mes PreC; HMT-3522; Primary-h Bone Periosteal; A431; Primary-h Brain EC; Primary-h UTFB; KLE; 143b OST; BALB/3T3; Primary-h Vase FB; LLC-PKI; Primary-h Vase Pericyte; BHK21-C13; Primary-Mammary EpiC; M.DUNNI; C4-2B; ZR-75; HEC-IB; Primary-h Gingiva Keratinocyte; U1 78; Primary-h HN Cancerous; Primary-mouse Mammary EpiC; Primary-h Keratinocyte; Primary-mouse Sciatic N Schwann; OVCA429; Primary-h Kidney EpiC; Primary-pig Esoph FB; MBA-15; Primary-pig Mandible FB-like; Primary-h Liver Cancerous; Primary-rabbit Bladder Uro; GD25beta1A; Primary-rabbit ID AnnulusC; HSC-T6; Primary-rabbit NP Neuronal; DOV 13; HEY; Primary-h Mammary FB; HTB-94; BZR-T33; Primary-chicken CorneaFB; MiaPaCa2; Primary-rat Mucosa Ensheathing; Primary-hOvaryFB; Primary-rat Salivary Acinar; Primary-h Ovary Oocyte; Primary-rat Testes Germ; Primary-h Pancreas Cancerous; Primary-chicken Embryo StC; Primary-h Pancreas Stellate Cells; Primary-sheep Carotid Artery FB; MLO-Y4;

Primary-chicken Retina SC-like; Primary-h Prostate Cancerous; Primary-chicken Ten TC; Primary-h Saph V Myo FB; Primary-Synoviocyte; MTLn3; Primary-Vase EC; Primary-h Skeletal Muscle Pre; RT4-D6P2T; C2; SCA-9; HOC-7; T31; Primary-h UC EpiC; TR146; HCS-2/8; EA.hy926; Primary-rat Ebryo; SW480; Primary-sheep Fetus CC; Primary-dog Pancreas Insulin; KS-IMM; BPH-1; Primary-rat Pancreas SC; M2139; RIN-5F; Primary-hGallbladderCancerous; E14/TG2a; M4E; HES3; GS; Primary-hConjunctivaFB; Primary-dogSaphVEC; LN CaP; Primary-dog Saph V SMC; M4T; Primary-h Fetus CC; BR-5; Primary-pig UT Uro; Primary-Hippocampus Neuronal; PE-•0041; Primary-dog Skin FB; Primary-rabbit Skeletal Muscle Myo-Blast; Primary-cowDenta 1pulp; CGR8; Primary-dog Teeth PDL; Primary-rat Fetus Hep; Primary-dog Tendon FB; Primary-rat Mammary; Primary-h Knee C; Primary-rat SMC; BRC6; Primary-sheep Artery FB; Primary-dog Vase EC; Primary-cow Mammary Alveolar; pZIP; 293 cell line; BMC9; Primary-h Lung Cancerous; SKOV-3; IOSE; TEC3; MCF-12A; Primary-rabbitBladderEpiC; Gli36DeltaEGFR; Primary-rabbit Conjunctiva EpiC; Primary-h Lung Neuronal; Primary-rabbit Endometrium EpiC; 1205Lu; Primary-rabbit MDSC; 3T3-A31; Primary-rabbit Tendon Tenocyte; MDA-MB-435; Primary-h Cancerous; Primary-cow EC; Primary-rat Cornea FB; Primary-EpiC; Primary-rat Fetal Cardiac; Primary-h Meninges Arachnoidal; COS-1; Primary-Eye; Primary-rat Liver Oval C; GLUTag-INS; Primary-rat Oral Mucosa Keratinocyte; GM3348; CRFK; 21NT; Primary-rat Testes EC; Primary-h Nasal FB; Primary-h Dura MaterSC; Primary-h Nasal OB; Primary-dog NP Neuronal; Primary-h Nasal Secretory; Primary-sheep Lung FB; AC-1M59; BHPrE1; MIN6; Primary-UT; MKN28; RAT-2; MLO-A5; RT1 12; CRL-2266; S91; GM5387; SK-ChA-1; Primary-horse CC; SPL201; Primary-horse Tendon FB; Primary-h Fetus Mes PreC; D283; Primary-pig Thyroid EpiC; H1299; Par-ClO; AE-6; Primary-rabbit Blood Platelet; Primary-goat Carotid EC; Primary-rabbit Bone OC; Primary-goat Carotid FB; Primary-cow Cornea FB-like; Primary-h Pancreas SC; Primary-rabbit CT Pericyte; Primary-goat Carotid SMC; Primary-rabbit Esophagus SMC; Primary-h Parotid Acinar; Primary-baboon Blood EC; A498; Primary-h Bronchi SMC; Primary-h Placenta SC; Primary-rabbit Sphincter SMC; Primary-cow Retina SC; 7F2; MM-Sv/HP; AlO; Primary-h Prostate StC; Primary-buffalo Embryo SC-like; Primary-h Salivary Cancerous; CHO-4; Primary-h Salivary Salisphere; Primary-rat Cortical Neuronal; H13; Primary-rat Embryo Neuronal; Primary-guinea pig Pancreas EpiC; Primary-rat Fetal OB; H144; CNE-2; MPC-11; 21PT; Primary-cow Synovium; Primary-rat Liver EC; Primary-cow Fetus CC; BEAS-2B; H2122; LM2-4; Detroit 551; C18-4; FLC4; Ishikawa; Primary-rat Skin Keratinocyte; H35; Primary-rat Tendon; Primary-h SMC; HTR8; Primary-h Synovial CC; E8.5; H460M; HL-60; MUM-2B; CRL-1213; MUM-2C; CRL-12424; W20-17; Lovo; Primary-dog Blood EC; Primary-sheep Nasal CC; HAK-2; Primary-sheep Skin FB; Primary-h Testes Sertoli; Primary-h Thyroid Cancerous; Primary-Trachea; Primary-h Trachea; LRM55; Primary-h UASC-like; Primary-Colon FB; Primary-hUASMC; r-CHO; HAT-7; RN22; HC-11; Primary-h Eye Vitreous; AEC2; S2-020; HCC1937; CRL-2020; AG1522; SCC-71; N18-RE-105; SK-N-AS; Primary-h Uterus SMC; SLMT-1; IMR-32; STO; NB4; Swan 71; Primary-h Alveolar Perosteum; Primary-dog Oral Mucosa EpiC; Primary-h Amnion EP; Primary-h Fetus Schwann; Primary-dog Bone OB; Primary-pig UTSMC; 184A1; Pane 1; NCTC 2544; 46C; Primary-cow Cornea EC; B6-RPE07; Primary-hamster EC; cBAL111; Primary-hamster Retina Neuronal; HEPA-1Clc7; NEB1; CCE; NHPrE1; Primary-rabbit ConjunctivaFB; 410; Hepa RG; Primary-Keratinocyte; PMC42-LA; Primary-dog Cartilage Synov; 21MT; NOR-P1; Primary-rabbit Endometrium StC; Primary-Lymphnode Lymphocyte; DLD-1; Primary-Lymphnode TCell; Primary-rabbit Lacrimal Gland Acinar; AB2.1; primary-rabbit Lung Pneumocyte; Primary-monkey Embryo; ES-2; Primary-monkey Kidney FB-like; Primary-rabbit Penis SMC; Primary-mouse Adipose StC; Primary-rabbit Skin FB; NR6; Primary-Blood SC; Primary-mouse BM Macrophage; 786-0; AT2; Primary-rat Adrenal Chromaffin; AT3; CCF-STTGI; Primary-mouse Bone Calvarial; Primary-rat Bladder Uro; HCT-8/E11; CE3; Primary-mouse Brain Neuronal; CFK2; Primary-mouse Breast Cancerous; L6; Primary-mouse Chondrocytes; HeyA8; Primary-mouse Colon EpiC; Primary-rat Cortical Astrocyte; Primary-dog CFB; Primary-buffalo Ovary EpiC; Primary-dog Cornea Chondrocyte; Primary-rat Embryo CM; Primary-mouse Embryo Neuronal; A2780; C5.1 8; Primary-dog MV EpiC; Primary-mouse Esophagus SC; Primary-rat Fetal Renal; HEKOO1; A357; EFO-27; Primary-chicken Bone OB; Primary-mouse Fetal Lung; Primary-rat Heart SC-like; Primary-mouse Germ; Primary-rat Kidney; EN Stem-A™; Primary-rat Lacrimal Acinar; U-251 MG; Primary-dog Myofibroblasts; A4-4; Primary-rat Liver SC-like; Primary-cow Brain EC; Primary-rat Lung FB; Primary-mouse Kidney Renal; BEL-7402; NT2; HIAE-101; Primary-h BM Mononuclear; Primary-rat Ovary; Primary-mouse Lymph FB-like; Primary-rat Pancreas Islets; Primary-dog Esophageal EpiC; Primary-rat Renal EpiC; Primary-mouse Mast; Primary-chicken Embryo Blastoderm; NTera2/cl.D1; G-415; Null; Primary-rat Small Intestine; Primary-mouse Ovary Cumulus C; Primary-rat Teeth SC-like; HEL-299; Primary-rat Tendon Tenocyte; KB; b-End-2; Primary-mouse Pancreas Insulin; Primary-rat Vase EC; Primary-mouse Salivary Salisphere; Primary-h Duodenum EpiC; Primary-h Bone Fetus OB; Primary-Respiratory EpiC; Primary-mouse Skeletal Muscle Myoblast; Primary-sheep Amniotic fluid; OC2; Primary-chicken Heart CM; Daudi; Primary-sheepArtery MyoFB; Primary-mouse SkinKeratinocyte; Primary-sheep Bone OB-like; Primary-mouse Small Intestine; Primary-chicken Heart ECM; Primary-mouse Spleen Tcell; LNZ308; Primary-mouse Teeth Odontoblast; Primary-sheep ID Annulus Fibrosus; Primary-mouse Testes SC; Primary-sheep Jugular Vein SMC; Primary-mouse Testes Sperm; Primary-sheep Lung SC; Primary-mouse UT Uro; Primary-sheep Saph VEC; Primary-mouse Uterus EpiC; Primary-sheep Skin EC; OCT-1; Primary-sheep Vase EC; HELF; Primary-sheep Vase SMC; CAC2; HL-7720; OPC1; Primary-Teeth PDL; Primary-dog Heart SC; Primary-UCB/Mononuclear; Primary-pig Artery Carotid EC; Primary-h Endometriotic CystStC; Primary-pig Artery Carotid SMC; Primary-Colon Cancerous; Primary-pig Artery Coronary SMC; QCE-6; Primary-pig Bladder FB; R221A; OSCORT; LS180; B35; RIF-1; Calu-1; RL-65; Calu-3; Primary-cow Adrenal ChrC; B5/EGFP; RT-112; Primary-pigEC; RW.4; Primary-pig ESC; S2-013; OVCAR-5; S5Y5; Primary-h Bone OC-like; SA87; INT-407; SAV-I; Primary-pig Fetus Hep; SCC-68; P69; HNPSV-1; CaSki; SK-C015; Primary-pig Iliac EC; SK-N-DZ; Hep2; SKOV3ip.1; Primary-pig Mandible Ameloblast; SNB 19; Primary-cow Joint Synovial; Primary-h Fetus FB; Primary-pig Mandible Odontoblast; SWI 353; Primary-pig NP Neuronal; SW948; Primary-pig Oral MucosaEpiC; CRL-2102; Primary-pig Pancreasislets; T4-2; Primary-pig PulmonarySMC; TE-85; Primary-pig Salivary Acinar; THP-1; Primary-pig SynoviumSC; BME-UV1; KG-1; D4T; HUES-9; Primary-mouse Hippocampus Neuronal; ECV304; NRK; Primary-mouse Kidney Mesangial; D407; 1OT1/2 cell line; and Primary-h Foreskin Melanocyte.

Figure 1B:
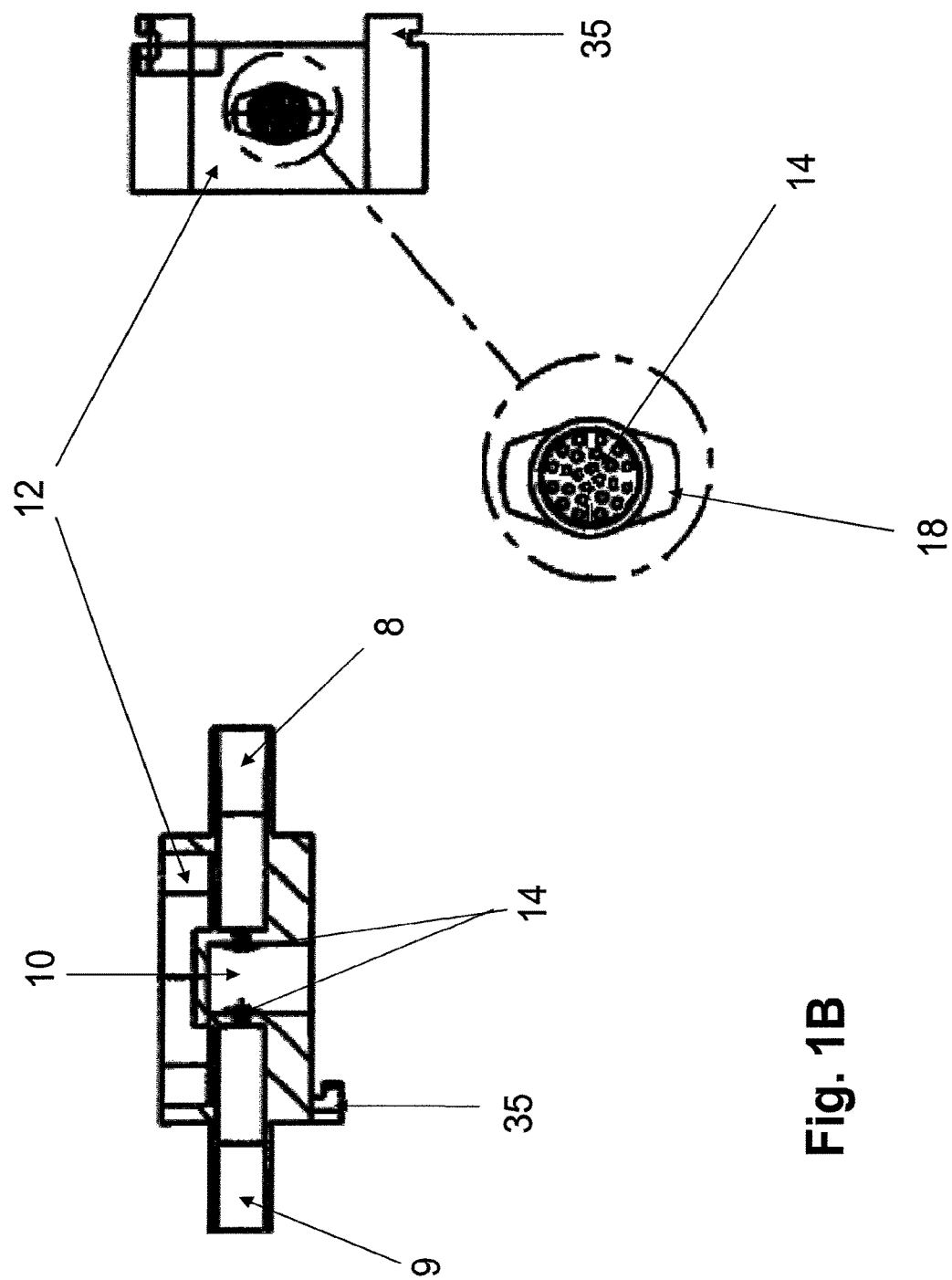

Referring to FIG. 1A and FIG. 1B, a view of one embodiment of the bioreactor system is illustrated. In one aspect, the bioreactor system 2 comprises at least one individual culture chamber 10, which is defined therein a cell module 12. The dimensions and overall size of a cell module 12, and culture chamber 10, are not critical to the invention. In general, a cell module 12 can be of a size so as to be handled and manipulated as desired, and so as to provide access to the culture chambers either through disassembly of the device, through a suitably located access port, or according to any other suitable method. As one skilled in the art will appreciate, the culture chamber 10 defined by the module 12 can generally be of any size as long as adequate for the assigned task. In one aspect, nutrient flow can be maintained throughout a three-dimensional cellular construct growing in the culture chamber 10, so as to prevent cell death at the construct center due to lack of nutrient supply.

Thus, in one aspect, one embodiment is a cell module 12. Though each cell module 12 of the embodiment illustrated in FIG. 1A and FIG. 1B can comprise a single culture chamber 10, or, optionally, a single cell module 12 can comprise multiple culture chambers. In the latter aspect, each culture chamber of the module can comprise individual access ports (described further below), so as to provide individualized flow through each culture chamber and independent control of the local environmental conditions in each culture chamber. While the materials from which the module 12 can be formed can generally be any moldable or otherwise formable material, the surface of the culture chamber 10, as well as any other surfaces of the module that may come into contact with the cells, nutrients, growth factors, or any other fluids or biochemicals that may contact the cells; should be of a suitable sterilizable, biocompatible material. In one particular embodiment, components of the system can also be formed so as to discourage cell anchorage at the surfaces.

It is also contemplated herein that the cell module 12 and the components that make up the cell module 12 can be constructed from a single mold rather than attaching individual pieces. That is, disclosed herein are bioreactor systems wherein each cell module comprises a monolithic construction. The advantage of such construction provides increased sterility and removes possibilities of leaks forming. Thus, in one aspect, the cell module 12 can be constructed of any material suitable to being formed in a mold.

In one embodiment two cell modules 12 can be selectively coupled via a compression fitting so form two culture chambers 10 that are adjoined and are in selective biological communication with each other. Thus, in one aspect, the cell modules 12 can comprise a means for sealingly engaging the top surface of one module with the top surface of another module. It is understood that once fully engaged, the two cell modules can selectively, and optionally releasably, lock into place. In one aspect, it is contemplated that the means for sealingly engaging the respective cell modules will cause a compressive force to be effected on the adjoined surfaces of the respective modules. It is understood that there are many means for sealingly engaging two cell modules 12. One such method is shown in FIG. 1A. In this aspect, a male compression fitting 35 can be configured to sealingly engage the fitting 36 to form a compression fitting. In one aspect, the fitting 36 can have a raised portion and the male compression fitting 35 an indentation that when aligned form a lock. It is understood that such an engagement means could be engaged using a press and twisting motion. It is further understood that said engagement means could be disengaged by twisting in the opposite direction. It is further understood that the cell module 12 comprises both the male compression fitting 35 and female fittings 36 on the same or opposing faces of the cell module 12. For example, the cell module 12 can comprise male compression fittings on one face and female fittings 36 on the opposite face. Alternatively, the cell module 12 can comprise male compression fittings 35 and female fittings 36 on the same face. It is understood that the placement of the male fittings 35 and female fittings 36 is such that compression and stability are maximized, for example, with male compression fittings 35 being at opposite corners or sides from each other but adjacent to female fittings 36 which are on opposite sides or corners from each other.

Alternatively, the two cell module system can comprise a first cell module 12 and a second cell module 12, wherein the first and second module comprise identical cell chambers 10, inlets, and outlets, but wherein the first cell module 12 comprises one or more male compression fittings and the second cell module 12 comprises one or more female fittings. For example, the first cell module 12 can comprise only male compression fittings 35 and the second cell module 12 can comprise only female fittings 36. In an alternative example, the top surface of the first cell module 12 can comprise a raised perimeter with a convex bevel located at the mid point to three fourths point on the interior wall of the raised perimeter. The top surface of the second cell module 12 can have a perimeter relief that is of a depth to receive the male fitting on the first cell module. Additionally, the relief on the second cell module 12 can have a concave indentation which can form a lock when the convex bevel of the first cell module 12 is engaged. Similarly, the first and second cell modules 12 can be threaded in such a manner to allow the first module to be screwed down on the second module.

Thus, in one aspect a cell culture system can comprise first and second cell modules 12 capable of engaging wherein the first and second cell module are identical and interchangeable. In another aspect, the cell culture system can comprise a first and second cell module 12, wherein the first and second cell module are not identical or interchangeable but capable of being engaged.

It is further contemplated that the cell culture systems disclosed herein can comprise one or more first and second cell modules. The cell culture systems can have cell modules 12 independently controlled or serially linked through the outlet of one first and second cell module to the inlet of a second first and second cell module. The connections of inlets and outlets to media source, reagents, or flow source can be regulated by valves or linked directly to said source. Alternatively when serial linking is used, the outlet of one cell module 12 can be directly linked to the inlet of a second cell module 12 or have a controlled connection such as with a valve.

The culture chamber 10 can generally be of a shape and size so as to cultivate living cells within the chamber. In one preferred embodiment, culture chamber 10 can be designed to accommodate a biomaterial scaffold within the culture chamber 10, while ensuring adequate nutrient flow throughout a cellular construct held in the culture chamber 10. For instance, a culture chamber 10 can be between about 3 mm and about 10 mm in any cross sectional direction. In another embodiment, the culture chamber can be greater than about 5 mm in any cross sectional direction. For instance, the chamber can be cylindrical in shape and about 6.5 mm in both cross sectional diameter and height The shape of culture chamber 10 is not critical to the invention, as long as flow can be maintained throughout a cellular construct held in the chamber.

It is understood that the formation of the culture chamber creates a volumetric reservoir or a size determined by the cross sectional direction and depth of the chamber. Accordingly, it is understood that the disclosed culture chambers 10 can be between 1 μL and 50 mL, 50 μL and 1 mL, 100 μL and 500 μL, or 250 μL or any volume therebetween. Typically the culture chamber is circular or oval in cross sectional shape. However, it is further understood that the cross sectional shape of the culture chamber 10 can also be hexagonal, heptagonal, octagonal, nonagonal, decagonal, hendecagonal, dodecagonal, or larger polygon in shape. Additionally, it is contemplated herein that the closed end of a cell culture chamber 10 can be flat or convex. It is understood that fewer angles and abrupt changes in plane encourages cells to avoid adhering to the walls of the culture chamber and reduce turbulence of fluids passing through the chamber. Thus, it is contemplated herein that the shape of the culture chamber can be selected based on the particular characteristics one of skill in the art desires to replicate.

In one aspect, the culture chamber 10 is defined by an open end port on the top surface of the cell module 12 and a closed end on the bottom surface of cell module 12. The open end allows for the addition for cell anchorage and cells and can be sealed by a membrane 23 (see FIG. 2). It is also contemplated that the culture chamber can be open at both ends and, in this aspect, the open ends of the culture chamber 10 are defined in the respective top and bottom surfaces of the cell module 12. In another aspect the culture chamber 10 is defined by an opened end port on both the top and bottom surface. As one skilled in the art will appreciate, when the culture chamber 10 is defined by two opened ports, the open ended ports can be closed by mating the cell module 12 with a second cell module 12 and placing a membrane between the respective cell culture chambers 10. Thus, in another aspect, disclosed herein are bioreactor systems further comprising at least one third cell module, wherein the third cell module comprises a cell chamber open at both ends, wherein the cell chamber of the third cell module is closed by sealingly engaging the first and second cell modules on opposite faces of the third cell module 12.

The system can also comprise a cell anchorage that can be contained in the culture chamber 10. The term "cell anchorage" as utilized herein refers to one or more articles upon which cells can attach and develop. For instance, the term "cell anchorage" can refer to a single continuous scaffold, multiple discrete scaffolds, or a combination thereof. The terms "cell anchorage," "cellular anchorage," and "anchorage" are intended to be synonymous. It is contemplated that any suitable cell anchorage as is generally known in the art can be located in the culture chamber 10 to provide anchorage sites for cells and to encourage the development of a three-dimensional cellular construct within the culture chamber 10.

For purposes of the present disclosure, the term continuous scaffold is herein defined to refer to a construct suitable for use as a cellular anchorage that can be utilized alone as a single, three-dimensional entity. A continuous scaffold is usually porous in nature and has a semi-fixed shape. Continuous scaffolds are well known in the art and can be formed of many materials, e.g., coral, collagen, calcium phosphates, synthetic polymers, and the like, and are usually pre-formed to a specific shape designed for the location in which they will be placed. Continuous scaffolds are usually seeded with the desired cells through absorption and cellular migration, often coupled with application of pressure through simple stirring, pulsatile perfusion methods or application of centrifugal force.

Discrete scaffolds are smaller entities, such as beads, rods, tubes, fragments, or the like, for example tubes for the formation of vascular tubes. When utilized as a cellular anchorage, a plurality of identical or a mixture of different discrete scaffolds can be loaded with cells and/or other agents and located within a void where the plurality of entities can function as a single cellular anchorage device. Exemplary discrete scaffolds suitable for use in the present invention that have been found particularly suitable for use in vivo are described in U.S. Pat. No. 6,991,652, which is incorporated herein in its entirety by reference. A cellular anchorage formed of a plurality of discrete scaffolds can be preferred in certain embodiments of the bioreactor system as discrete scaffolds can facilitate uniform cell distribution throughout the anchorage and can also allow good flow characteristics throughout the anchorage as well as encouraging the development of a three-dimensional cellular construct.

In one embodiment, for instance when considering a cellular anchorage including multiple discrete scaffolds, the anchorage can be seeded with cells following assembly and sterilization of the system. For example, an anchorage including multiple discrete scaffolds can be seeded in one operation or several sequential operations. Optionally, the anchorage can be pre-seeded, prior to assembly of the system. In one aspect, the anchorage can comprise a combination of both pre-seeded discrete scaffolds and discrete scaffolds that have not been seeded with cells prior to assembly of the bioreactor system.

The good flow characteristics possible throughout a plurality of discrete scaffolds can also provide for good transport of nutrients to and waste from the developing cells, and thus can encourage not only healthy growth and development of the individual cells throughout the anchorage, but can also encourage development of a unified three-dimensional cellular construct within the culture chamber. Thus, it is understood the scaffolds and matrices utilized herein can comprise shapes akin to real tissues with meaningful volumes.

The materials that are used in forming an anchorage can generally be any suitable biocompatible material. In one embodiment, the materials forming a cellular anchorage can be biodegradable. For instance, a cellular anchorage can comprise biodegradable synthetic polymeric scaffold materials such as, for example and without limitation, polylactide, chondroitin sulfate (a proteoglycan component), polyesters, polyethylene glycols, polycarbonates, polyvinyl alcohols, polyacrylamides, polyamides, polyacrylates, polyesters, polyetheresters, polymethacrylates, polyurethanes, polycaprolactone, polyphophazenes, polyorthoesters, polyglycolide, copolymers of lysine and lactic acid, copolymers of lysine-RGD and lactic acid, and the like, and copolymers of the same. Optionally, an anchorage can comprise naturally derived biodegradable materials including, but not limited to, chitosan, agarose, alginate, collagen, hyaluronic acid, and carrageenan (a carboxylated seaweed polysaccharide), demineralized bone matrix, and the like, and copolymers of the same.

It is contemplated that exemplary scaffold materials can comprise, at least partially and without limitation: Collagen; PLA/poly(lactide); PLGA/poly(lactic-co-glycolic acid); Chitosan; PCL/poly(e-caprolactone); Alginate/sodium alginate; PGA/poly(glycolide); Hydroxyapatite; Gelatin; Matrigel™; Fibrin; Acellular/Allogenic Tissue (all forms); Hyaluronic Acid; PEG/poly(ethylene glycol); Peptide; Silk Fibroin; Agarose/Agar; Calcium phosphate; PU/polyurethane; TCP/tri calcium phosphate; Fibronectin; PET/poly (ethylene terephthalate); Bioglass; PVA/Polyvinyl alcohol; Laminin; GAG/glycosaminoglycan; Cellulose; Titanium; DBP/demineralized bone powder; Silicone; PEGDA/PEG-diacrylate; Fibrinogen; Acellular/Allogenic Tissue-SIS; PDMS/polydimethylsiloxane; Acellular/Allogenic Tissue-Bone; ECM (in situ derived); Polyester; Elastin; PS/polystyrene; Glass; PBT/polybutylene terephthalate; Dextran; PEG/poly(ethylene glycol)-other modified forms; PES/polyethersulfone; PLL/poly-1-lysine; MWCNT/multiwalled carbon nanotube; PHBV/poly(hydroxybutyrate-co-hydroxyvalerate); Coral; Starch; PPF/poly(propylene:fumarate); PLCL/poly(lactide-co-e-caprolactone); Chondroitin Sulfate; PAM/polyacrylamide; PC/polycarbonate; PEUU/poly(ester urethane)urea; Calcium carbonate; Atelocollagen; PHB/poly(hydroxybutyrate); Polyglactin; Gelfoam®; Acellular/Allogenic Tissue-Vasculature; PuraMatrix™; PAA/poly(acrylic acid); PA/polyamide (Nylon); Clot; PDO/polydioxanone; PMMA/poly(methyl methacrylate) (acrylic); Acellular/Allogenic Tissue-Heart Valve; PHEMA/poly(hydroxyethyl methacrylate); PVF/polyvinyl formal; PGS/poly (glycerol sebacate); PEO/poly(ethylene oxide); Acellular/Allogenic Tissue-Cartilage; Pluronic® F-127; PHBHHx/PHB-co-hydroxyhexanoate; PHP/polyHIPE polymer; Polyphosphazene; Silicate; Poly-D-lysine; Poly peptide/MAXI; Aluminum oxide; PTFE/polytetrafluoroethylene; Silica/silicon dioxide; SWCNT/single-walled carbon nanotube; Cytomatrix® (Tantalum); PLG/poly(L-lactide-glycolide); ORMOCER®; POSS/polyhedral oligomeric silsesquioxanes; Acellular/Allogenic Tissue-Tendon; HEWL/Hen egg white lysozyme; Polyelectrolyte; Polyamidoamine; POC/poly(octanediol citrate); PEI/polyethyleneimine; Hyaff-11®; PTMC/poly(trimethylene carbonate); PAAm/Poly(allylamine); Polyester utethane; Lactose; PNiPAAm/poly(N-isopropylacrylamide); Polyurethane-urea; Keratin; Cyclic Acetal; NiPAAm; Poly HEMA-co-AEMA; PEI polyethylene (all forms); PLDLA/poly(L/D)lactide; Vitronectin; PDL/poly-D-lysine; Corn starch; TMP/trimethylolpropane; Poloxamine; Acellular/Allogenic Tissue-Skin; Gellan gum; PEMA/poly(ethyl methacrylate); Tantalum; DegraPol®; Silastic; Akermanite; Polyhydroxyalk: anoate; AlloDerm®; Polyanhydrides; Zirconium Oxide; Polyether; TMC/trimethylene carbonate; Sucrose; PEVA/poly(ethylene-vinyl alcohol); PMAA/poly(methacrylic acid); Hydrazides; Poly(diol citrate); PVDF/polyvinylidene fluoride; COBB/Ceramic Bovine Bone; PVLA/polyvinylbenzyl-D-lactoamide; PCU/poly(carbonate-urea)urethane; MBV; Chitin; Synthetic elastin; PBSu-DCH/diisocyanatohexane-extended poly(butyl); PANI/polyaniline; Polyprenol; Zein; Egg Shell Protein; EVA/Ethylene Vinyl Acetate; Gliadin; HPMC/hydroxypropyl methylcellulose; PE/phthalate ester; Thrombin; PP/Polypropylene; OptiCell™; PEEP/poly(ethyl ethylene phosphate); OCP/Octacalcium Phosphate; PEA/poly(ester amide); Aggrecan; Graphite; NovoSorb™; PLO/poly-L-ornithine; DOPE/dioleoyl phosphatidylethanolamine; ELP/Elastin-like polypeptide; LDI/lysine diisocyanate; PPC/poly (propylene carbonate); Plasma; Fe(C0)(5)/Iron pentacarbonyl; Asbestos; PPE/polyphosphoester; Azoamide; Triacrylate; PRP/platelet-rich plasma; Dextran•(modified forms); PGSA/poly(glycerol-co-sebacate)-acrylate; Polyorthoester; SPLE/sodium polyoxyethylene lauryl ether sulfate; Methacryloyloxy; TGA/thioglycolic acid; PCTC/poly(caprolactone-co-trimethylene carbonate; SU-8; SLG/sodium N-lauroyl-L-glutaminate; Polysulfone; Phosphophoryn; HEA ihydroxyethyl acrylate; PSSNa/poly(sodium styrene sulfonate); Carbon Foam; PFOB/perfluorooctyl bromide; Lecithin; Mebiol®; BHA/butylated hydorxyanisole; Surgisis®; OsSatura™; Skelite™; Cytodex™; COLLOSS®; E; Magnesium; PAN/polyacrylonitrile; HPMA/hydroxypropylmethacrylamide; Lutrol® F127; PDTEc/poly(desaminotyrosyl-tyrosineethyl esterc; Rayon (commercial product); Organo Clay; Portland Cement; Xyloglucan; Vaterite Composites (SPV); PRx/polyrotaxane; AW-AC/anti-washout apatite cement; Starch acetate; Nicotinamide; POR/poly-L-omithine hydrobromide; AM-co-VPA/acrylamide-co-vinyl phosphonic acid; Calcium Silicate; Carbylan GSX; Colchicine; GPTMS/glycidoxypropyltrimethoxysilane; Phosphorylcholine; PLE/polyoxyethylene lauryl ether; Tartaric acid; HPA/hydroxyphenylpropionic acid; PLVA/poly-N-p-vinylbenzyl-D-lactonamide; PEOT/polyethyle-neoxide-terephtalate; Adipose Tissue Powder; SLS/sodium lauryl sulfate; KLD-12 peptide; PDTOc/poly(desaminotyrosyl-tyrosine octylesterc; Si-TCP/silicate-substituted tricalcium phosphate; PCLF/polycaprolactone fumarate; PAMPS/poly (acrylamidomethylpropanesulfonicsodiu; Bio-Oss®; MGL/mono glyceryl laurate; DMA/fullerene C-60 dimalonic acid; THF/tetrahydrofuran; Polyphosphoester; Paper; Calcium-silicon; PPD/poly-p-dioxanone; BME/Basement Membrane Extract (generic); and OPF/oligo [poly(ethylene glycol) fumarate].

A biodegradable anchorage can comprise factors that can be released as the scaffold(s) degrade. For example, an anchorage can comprise within or on a scaffold one or more factors that can trigger cellular events. According to this aspect, as the scaffold(s) forming the cellular anchorage degrades, the factors can be released to interact with the cells. Referring again to FIG. 1A and FIG. 1B, in those embodiments including a cellular anchorage formed with a plurality of discrete scaffolds, a retaining mesh 14 can also be located within the culture chamber 10. The retaining mesh 14 can be formed of any suitable biocompatible material, such as polypropylene, for example, and can line at least a portion of a culture chamber 10, so as to prevent material loss during media perfusion of the culture chamber 10. Alternatively, the retaining mesh can be a located at the opening of the inlet and outlet of the culture chamber 10. The retaining mesh 14 can be an integral part of the inlet and outlet so as to be made of the same material and in the same form as the cell module 12 such that the retaining mesh 14 is not removable for the cell module 12. A porous retaining mesh 14 can generally have a porosity of a size so as to prevent the loss of individual discrete scaffolds within the culture chamber 10. For example, a retaining mesh 14 can have an average pore size of between about 10 μm and about 1 mm, between about 50 μm and about 700 μm, or between about 150 μm and about 500 μm.

Upon assembly of the bioreactor system, two (or more) culture chambers 10 can be aligned so as to be immediately adjacent to one another. In one aspect, to help create a fluid-proof seal of the system, a gasket 16 and a permeable membrane portion 23 can be positioned between the adjoining surfaces of the cell modules to selectively prevent fluid leakage from between the respective open ends (the respective ports of the culture chambers). In one aspect, the gasket 16 and the membrane portion 23 can be formed as a single integrated structure. It is contemplated that the membrane portion 23 of gasket 16 can be positioned between the respective ports adjoined culture chambers 10 and can have a porosity that can allow biochemical materials, for instance growth factors produced by a cell in one chamber, to pass through the membrane and into the adjoining chamber, where interaction can occur between the biochemical material produced in the first chamber and the cells contained in the second chamber.

Optionally, the two or more culture chambers 10 can be aligned with only the membrane portion 23 positioned between the adjoining surfaces of the cell modules and in over/underlying relationship to the respective ports of the adjoining chambers. In operation, by interlocking two cell modules 12, the membrane portion 23 can be compressed therebetween the adjoining surface to effect a fluid-proof seal around the ports of the culture chamber 10. Thus, in this exemplary aspect, the membrane acts as a gasket. In a further alternative embodiment, at least one of the cell modules can comprise a raised convex concentric ring which encircles the open end, the port, of the culture chamber 10 on the top surface of the cell module 12. fu this aspect, when the two cell modules are interlocked the added pressure placed on the raised area effects a seal on the membrane that is interposed therebetween. In a further aspect, the cell modules can comprise a male and female cell module where the male module comprises a raised convex concentric ring which encircles the open end, the port, of the culture chamber 10 on the top surface of the cell module 12 and the female cell module comprises a concave concentric ring which encircles the culture chamber 10 on the top surface of the female cell module 12. When the male and female cell modules are engaged, the male and female rings form a bight in the membrane creating a seal and aid in alignment of the culture chambers 12.

In bioreactor systems where a membrane is used without a gasket, the membrane becomes a gasket by compressing the membrane under the compression formed by the interlocking of two or more cell modules 12. Therefore, it is understood and herein contemplated that the membrane can comprise a compressible material that is conducive to the formation of a gasket. Such materials are well known to those of skill in the art.

In various aspects, it is contemplated that the membrane 23 can be a solid, non-porous, or semi-permeable (i.e., porous) membrane. The porosity can be small enough to prevent passage of the cells or cell extensions from one chamber to another. In particular, the membrane porosity can be predetermined so as to discourage physical contact between the cells held in adjacent chambers, and thus maintain isolation of the cell types. Suitable porosity for a membrane can be determined based upon specific characteristics of the system, for instance the nature of the cells to be cultured within the chamber(s). Such determination is well within the ability of one of ordinary skill in the art and thus is not discussed at length herein.

Additionally, the membrane 23 can comprise not only material that affects the transmission of physical parameters, but optical transmission as well. Thus, contemplated herein are membranes 23 wherein the membrane only allows the transmission of certain wavelengths of light to pass from one side of the membrane to the other or excludes specific wavelengths of light.

Alternatively, the membrane 23 can comprise a composite structure of both porous and non-porous or solid membranes, which allow the removal of one non-porous membrane while the other porous membrane remains in place between the culture chambers 10. In one aspect, the non-porous or solid membrane can be affixed to the porous membranes and separated from the porous membrane without needing to remove the semi-permeable membrane. Thus, the solid membrane allows for separate culturing conditions and media usage; whereas a porous membrane allows for the passage of biochemical materials. In another aspect, the membrane 23 comprising a porous and solid or nonporous membrane can be placed between adjoined culture chambers to allow for separate culture conditions and after a period of time the solid or non-porous membrane can be removed to allow for passage of biochemical materials.

In another alternative, the membrane 23 can comprise a biodegradable material. Through the use of a biodegradable material for the membrane 23, porosity can be electively increased over the course of the usage of the membrane. For example, a non-, porous membrane 23 made of biodegradable material can be used which prevents the exchange of culture conditions. In operation, as the material is used, the membrane degrades allowing for the exchange of biochemical materials. In a further alternative, the membrane 23 can comprise biodegradable and non-biodegradable material such as a porous non-biodegradable membrane where the pores are sealed with a biodegradable material or coating. As the biodegradable material or coating is dissolved, the non-degradable porous membrane is revealed.

In yet another alternative, the membrane 23 can comprise a porosity large enough to allow for the passage of cells between culture chambers 10. For example, the membrane can comprise pores from 0.05 µm to 100 µm, 0.1 µm to 20 µm, 1 to 10 µm, 1 to 5 µm, or 3 µm. Thus, examples of pore sizes for membrane 23, include but are not limited to 0.2 µm, 0.45 µm, 1 µm, 3 µm, and 8 µm. Through the use of such a porous membrane 23, cell migration/invasion assays can be performed that look at the effect of chemokines, cytokines, morphology, electricity, pressure, or modulators on the migratory process. Thus, in one aspect, a porous membrane 23, can be used to screen for modulators of cellular migration/invasion.

Physical isolation of cellular contents of adjacent chambers can also be encouraged through selection of membrane materials. In one aspect, materials used to form the membrane 23 can be those that discourage anchorage of cells onto the membrane 23. Attachment of cells to the membrane 23 can be discouraged to prevent physical contact between cells held in adjacent culture chambers as well as to prevent interference with flow between the adjacent chambers. Flow interference could interfere with the biochemical communication between the adjacent culture chambers. One exemplary material that can discourage cellular attachment is a polymer, such as, for example and without limitation, a polycarbonate membrane. Other suitable materials generally known to those of skill in the art comprise but are not limited to polyvinyl, polypropylene, polyethersulfone, Polyvinylidene Fluoride (PVDF), polycarbonate, polyolefin, and polytetrafluoroethylene (PTFE). Examples of suitable membranes can be purchased directly from Millipore, Pall, Whatmann, and Sartorious.

In another embodiment the cells contained in a culture chamber 10 can be maintained at a distance from the membrane 23 to discourage physical contact between cells held in adjacent culture chambers. For instance, in this example, retaining mesh 14 can be located between a cell anchorage held in a culture chamber and the membrane located between two adjacent chambers. The width of the retaining mesh 14 can prevent contact of the cells with the membrane 23. Optionally, the retaining mesh 14 can be at a distance from the membrane 23, providing additional separation between the membrane 23 and cells held in the culture chamber 10. In another embodiment, a continuous scaffold can be located in a culture chamber 10 at a distance from the membrane 23 so as to discourage physical contact between the cells held in the culture chamber and the membrane 23. While a preferred distance between the membrane 23 and cells held in the chamber will vary depending upon the specific characteristics of the system as well as the cells to be cultured in the system, in general, the distance between the two can be at least about 100 microns.

Each culture chamber 10 of the system can comprise the capability for independent flow control through the chamber. For example, and referring again to FIG. 1A and FIG. 1B, each individual culture chamber 10 can comprise an inlet 8 and an outlet 9 through which medium can flow. In this exemplary aspect, the inlet 8 and outlet 9 can be connected to medium perfusion tubing via quick-disconnect luers 18 and stopcock valves, but this particular arrangement is not a requirement of the invention, and any suitable connection and perfusion system as is generally known in the art can be utilized. In another embodiment, the connection can be an integral portion of a single formed module 12. For example, the luers 18 can be formed at the outward ends of the inlet 8 and outlet 9 as shown in FIG. 1A and FIG. 1B. It is understood and herein contemplated that other means for attaching tubing and stopcock valves are well known in the art and can be used in the present invention as an alternative to a luer lock. Such attachment mechanisms comprise but are not limited to compression fittings, threaded fittings, and friction.

It is contemplated that at least portions of the respective inlet 8 and outlet 9 can be straight or can comprise one or more bends. It is understood that the inlet 8 and outlet 9 do not have to line up within the culture chamber 10, but can be situated at opposing ends (i.e., one at the top and another the bottom as reflected in the middle module in FIG. 4). It is contemplated that the respective shapes of the inlet and outlet can be configured to affect the desired flow characteristics within the chamber.

Figure 2:
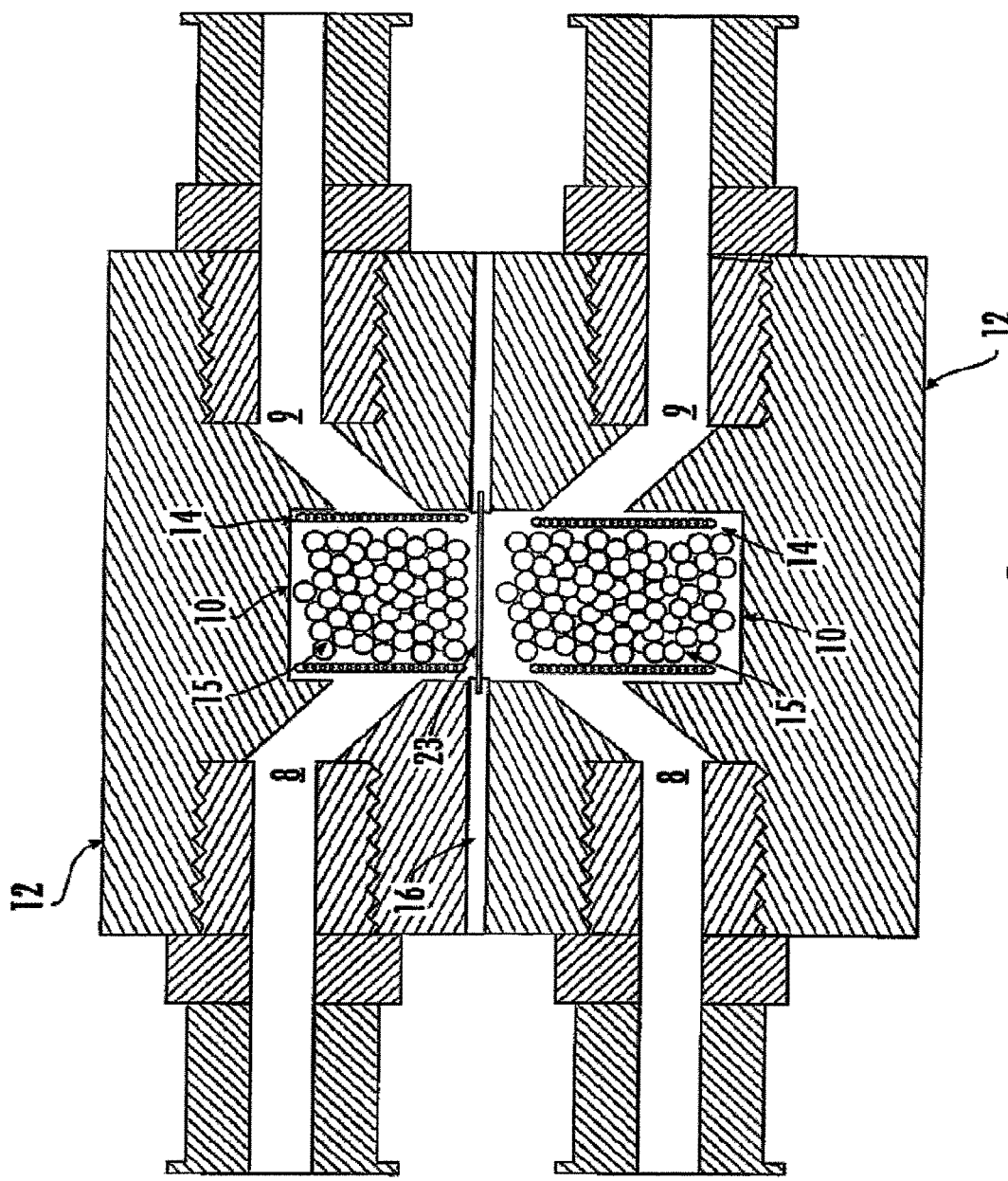
FIG. 2 is a schematic diagram of the embodiment of FIG. 1 following assembly such that the two cell modules are adjacent and allow biochemical communication between cells held in the two adjacent modules.

Referring to FIG. 2, one aspect of a pair of adjoined modules 12 following assembly is shown. As can be seen, the embodiment comprises two modules 12, each of which comprises a single culture chamber 10. Upon assembly, the two culture chambers 10 are aligned with the permeable membrane portion 23 of gasket 16 positioned therebetween the ports of the culture chambers. In this particular embodiment, a plurality of discrete scaffolds 15 has been located within each of the two culture chambers 10 as a cellular anchorage. In addition, each culture chamber 10 can be lined with a retaining mesh 14, as shown. Upon assembly, desired media can be independently perfused through each culture chamber 10 via the separate inlets 8 and outlets 9.

Figure 3:
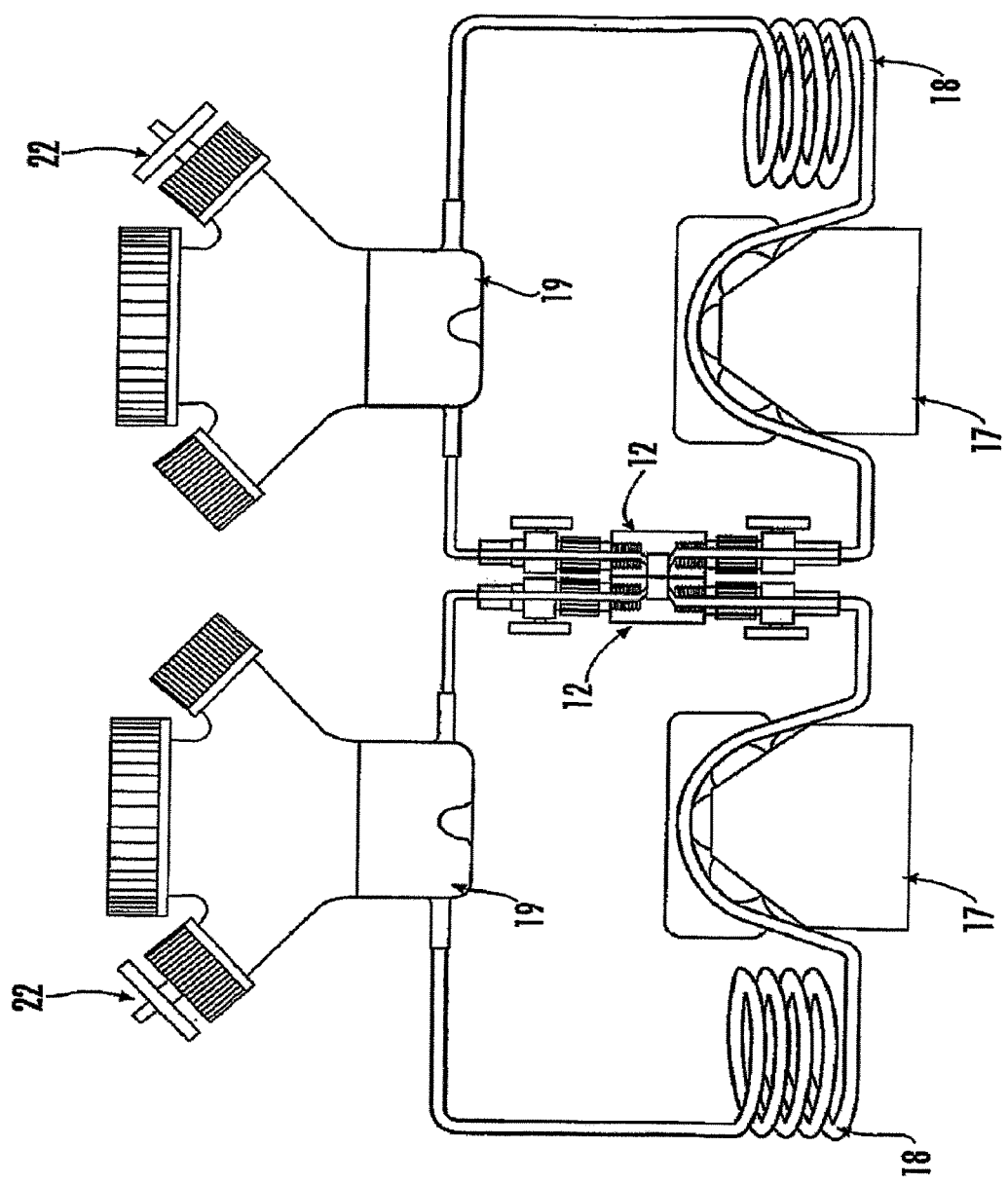

FIG. 3 illustrates one embodiment of a bioreactor system according to the present invention. This aspect comprises two assembled modules 12, such as those illustrated in FIG. 2, each in line in a flow circuit that is completely independent of the other that includes a pump 17, for instance a peristaltic pump and a media container 19. In this aspect, gas exchange can be facilitated by two methods, including a first method utilizing a coiled length of a gas permeable tubing 18 such as, for example, a platinum-cured silicone tubing, as well as a second method including an air filter 22 located, in this aspect, at the media container 19. Any gas exchange method as is known can alternatively be utilized, however.

One skilled in the art will appreciate that one of the many benefits of the disclosed invention is the versatility of the system and cell modules. For example, in the bioreactor system illustrated in FIG. 3, the design attributes allow convenient and flexible reversal of the perfusion flow for a particular experimental protocol. In addition, the disclosed bioreactor systems can be utilized to allow biochemical communication with physical separation between two or more different cell types for a variety of applications including, for example and without limitation, bone development (osteocyte/preosteoblast or stem cell/preosteoclast), breast tissue replacement (preadipocyte/endothelial), stem cell research (stem cells/feeder cells), and regeneration or replacement of damaged liver cells (hepatocyte/endothelial). Due to the liver's significant role in drug metabolism, hepatocytes are the most relevant cell type for many drug discovery applications. Unfortunately, primary hepatocytes cultured in monolayer often lose phenotype-specific functionality and undergo apoptosis. Biosynthesis of drug-metabolizing enzymes, essential for pharmaceutical toxicity assays, is among the first functions to be lost. Hepatocyte cell lines have similar drawbacks, ranging from significant to complete loss of important CYP-related enzyme functionality. These and other cell culture challenges require advanced solutions.

It is understood and herein contemplated that cell migration and invasion are critical aspects to the development and proliferation of cancer. Additionally, it is further understood that the disclosed bioreactor systems are ideal for the identification of agents that affect cell migration, proliferation, cell invasion and adherence. Accordingly the disclosed bioreactor systems can be used in methods to screen for agents that modulate cancer. Thus, disclosed herein are methods of screening for an agent that inhibits a cancer comprising culturing cancer cells in a first cell chamber 10 of a first cell module 12, administering an agent into a second cell chamber 10 of a second cell module 12, wherein the first and second cell chambers are separated by a membrane 23, and wherein an agent that inhibits proliferation, migration, or invasion of cells from the first cell chamber 10 across the membrane 23 into the second cell chamber 10 is an agent that inhibits cancer.

It is understood that the cell cultured in the first cell chamber 10 can be from a cell line or obtained from a biopsy or other tissue sample. It is further understood that the cancer can be selected from the group of cancers consisting of lymphoma, B cell lymphoma, T cell lymphoma, mycosis fungoides, Hodgkin's Disease, myeloid leukemia, bladder cancer, brain cancer, nervous system cancer, head and neck cancer, squamous cell carcinoma of head and neck, kidney cancer, lung cancers such as small cell lung cancer and non-small cell lung cancer, neuroblastoma/glioblastoma, ovarian cancer, pancreatic cancer, prostate cancer, skin cancer, liver cancer, melanoma, squamous cell carcinomas of the mouth, throat, larynx, and lung, colon cancer, cervical cancer, cervical carcinoma, breast cancer, and epithelial cancer, renal cancer, genitourinary cancer, pulmonary cancer, esophageal carcinoma, head and neck carcinoma, large bowel cancer, hematopoietic cancers; testicular cancer; colon and rectal cancers, prostatic cancer, or pancreatic cancer.

Figure 4:
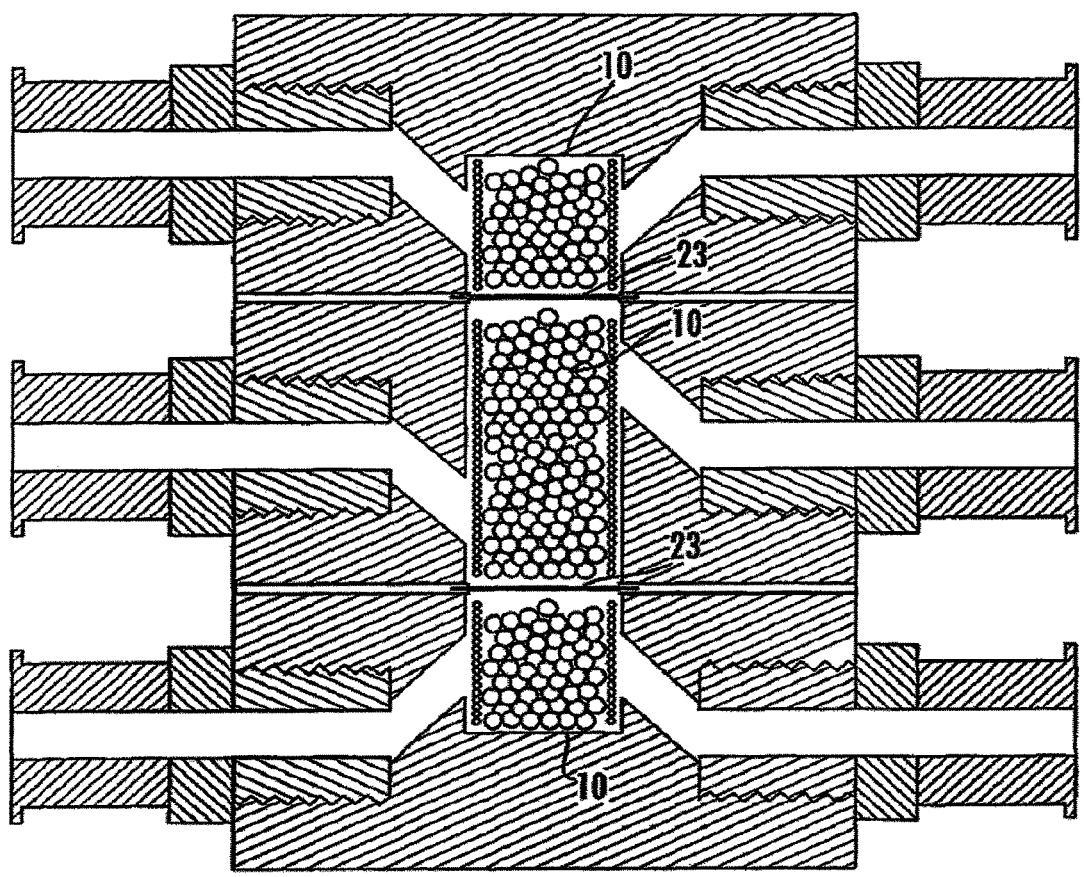
FIG. 4 is a schematic of a bioreactor system as herein disclosed including multiple cell culture chambers in biochemical communication with one another.

The bioreactor systems are not limited to single culture bioreactor systems or co-culture bioreactor systems in which only two independently controlled culture chambers are located adjacent to one another. In other aspects, additional cell modules can be selectively added to the bioreactor system such that a single culture chamber can be in selective biochemical communication with the contents of two or more other culture chambers. For example, a third chamber can house cells that can be in biochemical communication with the first culture chamber, optionally with a membrane separating the first and third chambers, though this aspect is not a requirement of the system such as for example in the instance stacked arrangement as illustrated in FIG. 4.

In one aspect, it is contemplated that the number of additional third chambers, which can be interior cell modules 12, which can be employed is not limited to a single interior cell module (i.e., three total cell modules 12 (one interior cell module and two end cell modules)), but can comprise 2, 3, 4, 5, 6, 7, 8, 9, 10 or more interior cell modules (i.e., 4, 5, 6, 7, 8, 9, 10, 11, 12, or more total cell modules 12 respectively). Thus, as a further embodiment disclosed herein are cell modules 12 that can be utilized as interior cell modules in a stacked configuration. Such interior cell modules 12 can comprise two top surfaces. Because the interior cell modules 12 comprise two top surfaces, the culture chamber 10 of these modules is open at both ends to allow for biochemical passage between the interior module and each of the exterior modules. As with the exterior cell modules, the top surface of the interior cell modules 12 can comprise means of sealingly engaging the top surface of other cell modules 12. Thus, it is contemplated herein that both of the top surfaces of the interior module 12 can comprise female fittings, male compression fittings, or a combination of both on each surface. Moreover, it is understood that the top surfaces of the interior cell module 12 can be identical or comprise an orientation with a male and a female end.

In another embodiment, one or more of the culture chambers of the system can be designed so as to provide the capability of subjecting the interior of the culture chamber to variable dynamic mechanical stimuli such as mechanical loading or variation in fluid flow through the culture chamber in order to vary the associated stress on the developing cells. Additionally one or more culture chambers of the system can be designed as to provide the capability of subjecting the interior of the culture chamber to electric current or a light source. Such an embodiment can be utilized to, for instance, trigger differentiation and development of stem cells contained in a culture chamber. In addition, cyclical hydrostatic loading patterns can be established, if desired, by simply cycling the pressurized fluid through the pressure chamber 24 through use of a solenoid valve and a time-delay relay, computer automation, or any other method that is generally known to one of ordinary skill in the art. Also, electrical currents can be provided through the use of an electrical probe in culture chamber of an adjacent cell module 12.

Figure 5:
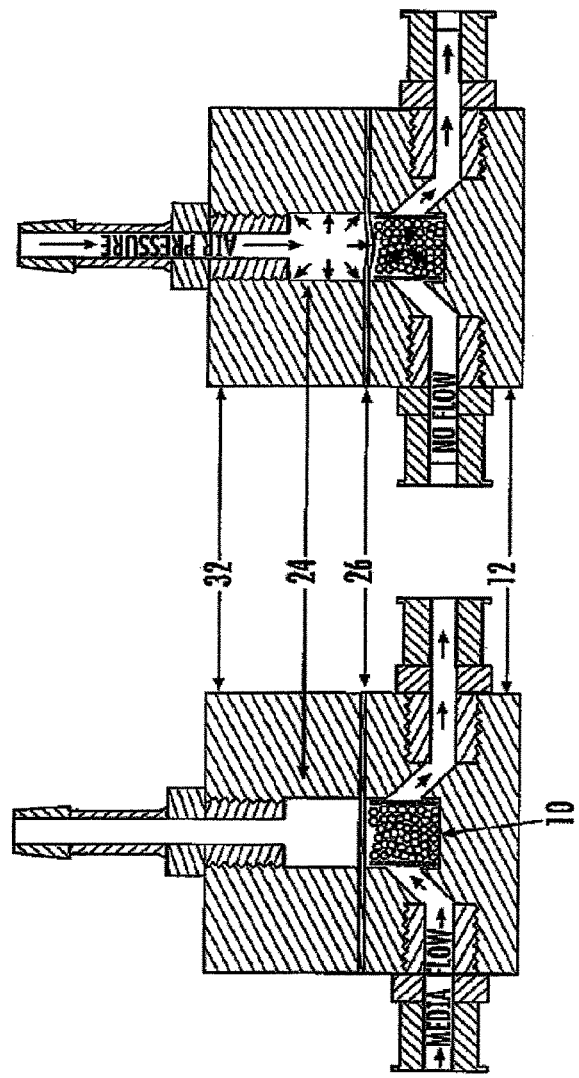
FIG. 5A and FIG. 5B illustrates another embodiment of the bioreactor system in which at least one of the cell modules of the bioreactor system can be subjected to periodic variation in hydrostatic pressure.

For example, according to one aspect, as illustrated in FIG. 5, a cell module 12 can be located immediately adjacent to a second cell module (not shown in FIG. 5), as described above. In addition, the cell module 12 can, on a second side of the module 12, be aligned with a pressure module 32 that can be utilized to vary the hydrostatic pressure on the contents of the culture chamber 10. According to this embodiment, the culture chamber 10 can be aligned with a pressure chamber 24 defined by pressure module 32, and the two adjacent chambers 10, 24 can be separated by an impermeable diaphragm 26. The introduction of pressurized fluid, e.g., air, into the pressure chamber 24, can deflect the diaphragm 26, as shown in FIG. 5B, and transfer the pressure to the volume of fluid in the culture chamber 10. In one embodiment, fluid flow through the culture chamber 10, as well as through other adjacent culture chambers, can be stopped prior to pressurizing the system, so as to develop a fixed volume of fluid within the affected portion of the system.

Such an embodiment may be particular beneficial in orthopedic related research studies. This system can provide improved ex vivo simulation of the physiological in vivo environment for bone that comprises both hydrostatic compression and perfusion fluid flow as a result of normal skeletal loading. For example, in one embodiment of the system, a hydrostatic loading cycle of 0.5 Hz and fluid pressures exceeding 300 kPa can be demonstrated. These values closely approximate those found in the lacunar-canalicular porosity of the human femur during normal gait, i.e., 0.5-2.0 Hz and 270 kPa.

In another embodiment, each cell module can be designed to allow for the direct sampling and observation of the culture chamber such as optical and spectrophotometric analysis. Such designs can comprise but are not limited to optically transmissive culture chamber 10 such that the bottom of the well of the culture chamber comprises optical glass or plastic (i.e., a cell module comprising optically transmissible material). Thus, a microscope can directly visualize the culture chamber 10 by focusing through the optically transmissive culture chamber on the bottom side of the cell module 12. Additionally, high resolution and three-dimensional imaging modalities including, but not limited to, laser confocal microscopy, multiphoton microscopy, optical coherence tomography, and nuclear magnetic resonance can be used to visualize the cell culture. The cell module 12 can be made from opaque material, for example and without limitation, the cell module can be made from opaque white material for luminescent detection or opaque black material for fluorescent detection to effectively limit endogenous background signal. Additionally, the cell module 12 can comprise translucent, photoreactive, or optically filtering glass or polymers. For example, the cell module 12 can comprise a polymer that allows the passage of certain wavelengths of light or filters out ultraviolet light. Similarly, the culture chambers can comprise an inlet through which an analytical probe may be inserted.

It is understood that when sampling an observation of culture chamber is undertaken, it can be useful to provide a mechanism for securing the cell module 12 on any device used for observation such as a microscope or plate reader such as a spectrometer. Thus, disclosed herein are cell modules mounted in a microscope stage adaptor (FIG. 23). Also disclosed are cell modules 12 mounted to well plate adaptor for use in instrumentation, i.e., spectrometer plate reader (FIG. 24).

In yet another embodiment, an electrical current can be provided to the interior of a culture chamber 10 through the use of a piezoelectric membrane 23. The piezoelectric membrane upon compression generates an electric current which is supplied to the culture chamber. In an alternative aspect, the electric current can be supplied through the use of cell anchorage constructed with a piezoelectric material. For example, as pressure is applied through the introduction of a pressurized fluid, an electrical current is emitted from the cell anchorage. Alternatively, the bioreactor systems disclosed herein can comprise an electrically charging or piezoelectric scaffold.

In various aspects, multiple independent bioreactor systems can be provided that can incorporate various combinations of experimental stimuli, which can provide real time comparisons of the differing stimuli on the developing cellular constructs.

In a further aspect, a bank of multiple and identical systems can be established that can provide replication of a single experimental procedure and/or to provide larger cumulative amounts of the product cells that are grown, developed or otherwise produced within each of the individual culture chambers.

It is contemplated that the disclosed culture systems can be incorporated into a singular instrument to allow for the control of temperature, gas exchange, media contents and flow rate, external and mechanical stresses, and endpoint analysis. The instrumentation can comprise multiple modular components each designed to accomplish a specific task. Thus, for example, the disclosed instrumentation can comprise one or more of a means for seeding cells onto anchorages, a means for controlling the flow of media, a means for adding or changing media, a means for subjecting the culture to mechanical stress or pressure, an analytical probe, and a device for manipulating the parameters of the various modules as well as collecting and analyzing data (for example, a computer and a computer program designed to accomplish these tasks).

The culture systems disclosed herein have many uses known to those of skill in the art. For example, the disclosed culture systems and cell modules can be used in tissue engineering where a 3D bioreactor is useful to properly model tissue.

Example 1

Cell Culture: A 3T3 mouse fibroblast cell line (available from ATCC, Manassas, Va.) was used in three studies (numbered 1-3 below) to examine cell viability when subjected to perfusion fluid flow in a system. A fourth study (Study 4) used a D1 cell line (ATCC) of adult mouse bone marrow stromal cells and incorporated hydrostatic compression in addition to the perfusion flow. The D1 cell line was selected due to its demonstrated multi-potent potential including favorable osteogenic properties.

Anchorage Fabrication: Multiple discrete poly-L-lactide (PLL) hollow beads with an average diameter of 0.8 mm served as the discrete tissue engineering scaffolds for all studies. Briefly, scaffold fabrication was completed using solvent emulsion techniques, beginning with an 8% (m/v) solution of Purasorb polylactide pellets (Cargill, Minneapolis, Minn.) and dichloromethane (Mallinckrodt Baker, Phillipsburg, N.J.). A quantity of 5 ml of PLL solution was dispensed, using a 20 cc glass syringe (BD, Franklin Lakes, N.J.) and 16-gauge needle (BD), into 500 ml of a stirred 0.1% aqueous solution of polyvinyl alcohol (PVA) (Sigma-Aldrich, St. Louis, Mo.). PVA solution in the amount of 300 ml was siphoned out of the beaker, after which, 200 ml of 2% isopropyl alcohol solution (VWR, West Chester, Pa.) was added. Following three minutes of stirring, 300 ml of solution was siphoned out and 400 ml of PVA solution was added back to the remaining 100 ml volume. The total volume of 500 ml was then stirred for three minutes, resulting in PLL bead formation. The hollow beads were strained from the solution and allowed to dry under vacuum to remove any residual solvent.

Modular bioreactor assembly was completed with the inclusion of a porous volume of 0.2 ml of PLL hollow beads within a culture chamber. Four sets of clamping socket screws, washers and nuts were used to form a tightly sealed assembly. The assembled bioreactor, including adjacent luers, stopcock valves and enclosed PLL beads, was sterilized with ethylene oxide gas at room temperature and degassed for several days under 25 inches Hg vacuum. Flow circuit tubing and quick-disconnect luers were also sterilized with ethylene oxide gas while the medium storage bottle was autoclaved.

The complete bioreactor flow circuit including a single cell module located immediately adjacent to a single pressure module such as that illustrated in FIG. 5 but with only a single culture chamber, was assembled in a standard laminar flow hood to prevent contamination. A volume of 60 ml of medium was added to the storage bottle. Initial culture medium for studies 1-3 consisted of Dulbecco's Modified Eagle's Medium (DMEM) (Invitrogen, Carlsbad, Calif.) supplemented with 10% fetal bovine serum (FBS) (Mediatech, Herndon, Va.), 5 ml antibiotic/antimycotic (Invitrogen), 1 ml fungizone (Invitrogen), 5 ml L glutamine (Invitrogen) and 10 pg fibroblast growth factor (Fisher): Initial culture medium used for study 4 was Dulbecco's Modified Eagle's Medium (ATCC) supplemented with 10% FBS. For all studies, the system was primed with medium to prewet the PLL beads prior to cell seeding. Cell seeding was accomplished by pipetting the appropriate cell suspension into the medium storage bottle and then allowing the system to perfuse the cells through the flow circuit to the discrete scaffolds within the cell module. The entire perfusion flow circuit was contained in an incubator that was maintained at 37° C. and 5% $CO_2$. Each of the four preliminary studies differed either in cell type, quantity, passage, duration or mechanical stimulus as described below in Table 1.

TABLE 1

| Study | Cell Type | Passage | Cell Seeding (per ml scaffold volume) | Cell Quantity Seeded | Duration | Mechanical Stimulus |
| --- | --- | --- | --- | --- | --- | --- |
| 1 | 3T3 | 37 | 1.2E7 | 2.4E6 | 7 days | Perfusion |
| 2 | 3T3 | 29 | 3.0E6 | 6.0E5 | 21 days | Perfusion |
| 3 | 3T3 | 31 | 3.0E6 | 6.0E5 | 21 days | Perfusion |
| 4 | DI | 24 | 3.0E6 | 6.0E5 | 28 days | Perfusion & Hydrostatic |

Study 1 provided initial observations regarding metabolism and viability of cells cultured within the confines of the culture chamber. A medium perfusion volumetric flow rate of 4.8 ml per minute was continuous throughout the seven-day duration. The medium was not changed for the seven-day duration of the study. Lactic acid and glucose levels were measured at days 0 and 7 using a YSI 2700 SELECT Biochemistry Analyzer (YSI, Yellow Springs, Ohio). Visual inspection of live fibroblast attachment to the PLL beads was demonstrated at day 7 through the use of a LIVE/DEAD® Viability/Cytotoxicity Kit (Invitrogen) and fluorescent microscopy. A seven-day acellular control study was conducted in parallel to confirm that rising lactic acid levels were due to cell metabolic activity and not PLL hydrolysis.

Studies 2 and 3 extended the culture time to 21 days and provided opportunity to refine endpoint assay techniques. As in Study 1, the volumetric flow rate of 4.8 ml per minute was continuous for the 21-day duration with the exception of brief periods of medium changes and aliquot retrieval. Medium aliquots were taken every two days, beginning on day 4, and complete medium changes occurred on days 8 and 16. Aliquots were monitored for metabolic solute levels, and live/dead fluorescent microscopy was completed on day 21. Unlike previous studies, study 4 incorporated hydrostatic compression in the experimental protocol beginning on day 4. Daily routine involved 8 hours of cyclic hydrostatic compression, approximately 330 kPa at 0.1 Hz (5 seconds on, 5 seconds off), followed by 16 hours of continuous perfusion flow at 4.8 ml per minute. Hydrostatic compression was interrupted after 4 hours with 5 minutes of perfusion flow to deliver fresh nutrients to the cells and prevent the buildup of waste products. A control system was used that did not receive hydrostatic compression loading. The control system's stopcock valves adjacent to the cell module were closed during the eight-hour hydrostatic segment but no pressure was applied. The inclusion of D1 adult mouse bone marrow stromal cells was strategic due to the demonstrated osteogenic characteristics. These properties provided opportunities to observe changes in phenotype differentiation in response to the applied mechanical loading regimens. Beginning at day 3, osteogenic media for both the experimental and control systems were supplemented with 50 pg/ml L-ascorbic acid (Sigma) and 10 mMI3-glycerophosphate (Sigma). Assays commonly used to evaluate osteogenic differentiation, including alkaline phosphatase activity, calcium content and total protein, were practiced for application in future experiments. Metabolic activity was observed through assessment of medium aliquots as well as relative AlamarBlue™ (Biosource, Camarillo, Calif.) fluorescent emission.

The graphs of FIGS. 6-10 represent mean±standard error of the mean with n=1, where n represents the number of replications of a given study. Nested measurements were made within each study at the respective time points; thus, variability is due to subsampling within the experimental assay. Therefore, no statistical comparisons could be made for the preliminary experiments. Microsoft Excel was used for all numerical analysis.

Figure 6:
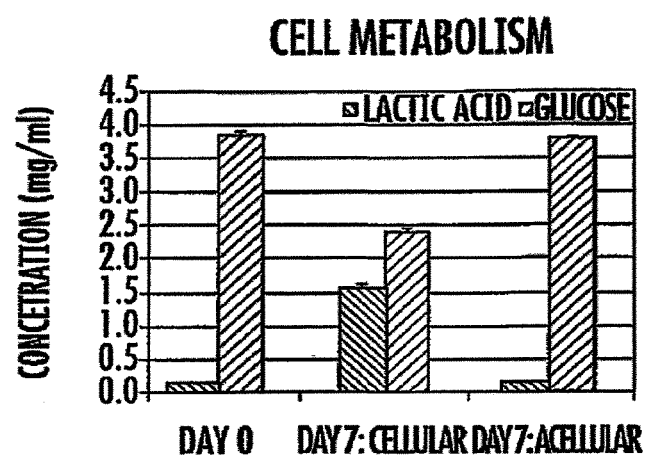
FIG. 6 illustrates cellular metabolic activity over a seven-day duration for bioreactor cell study 1 as described in Example 1.
Figure 7:
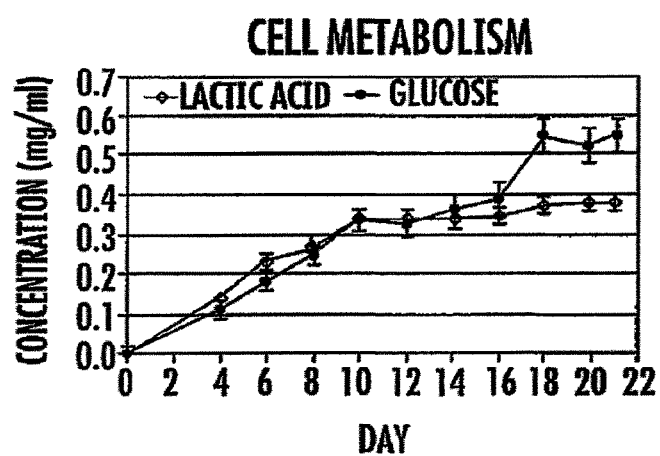
FIG. 7 illustrates average cumulative metabolic data over 21-day duration for bioreactor cell studies 2 and 3 as described in Example 1.
Figure 8:
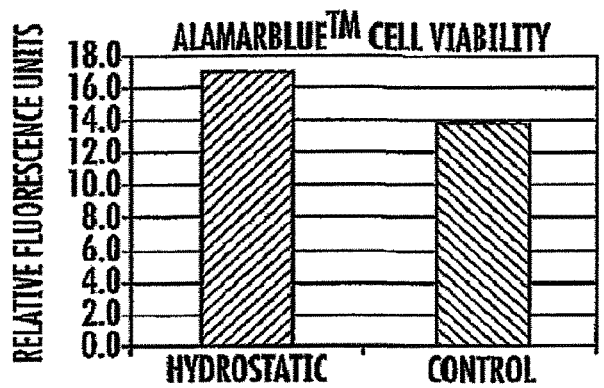
FIG. 8 illustrates cell viability on day 28 for the experimental and control setups for bioreactor cell study 4 as described in Example 1.
Figure 9:
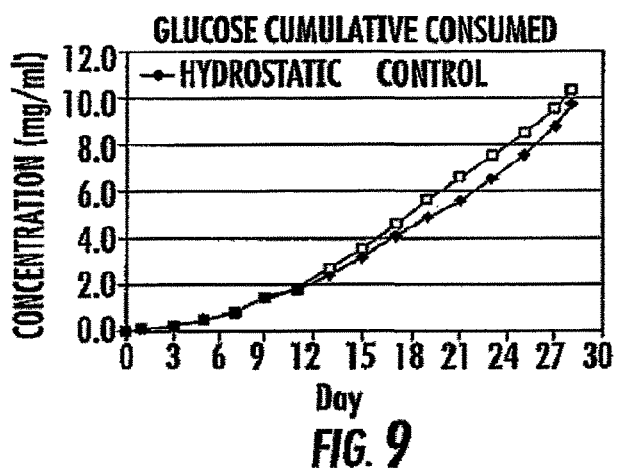
FIG. 9 illustrates cumulative glucose consumed over 28-day duration for bioreactor cell study 4 as described in Example 1.
Figure 10:
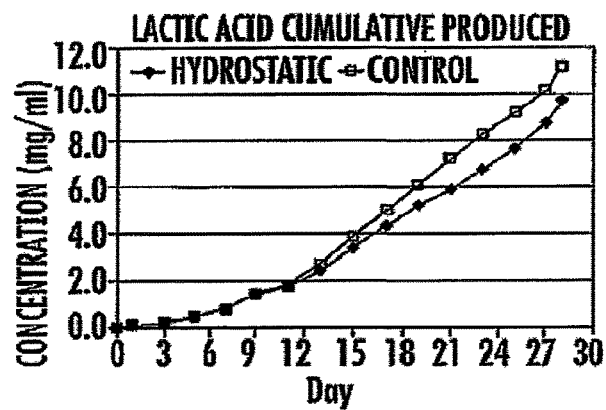
FIG. 10 illustrates cumulative lactic acid produced over 28-day duration for bioreactor cell study 4 as described in Example 1.
Figure 11:
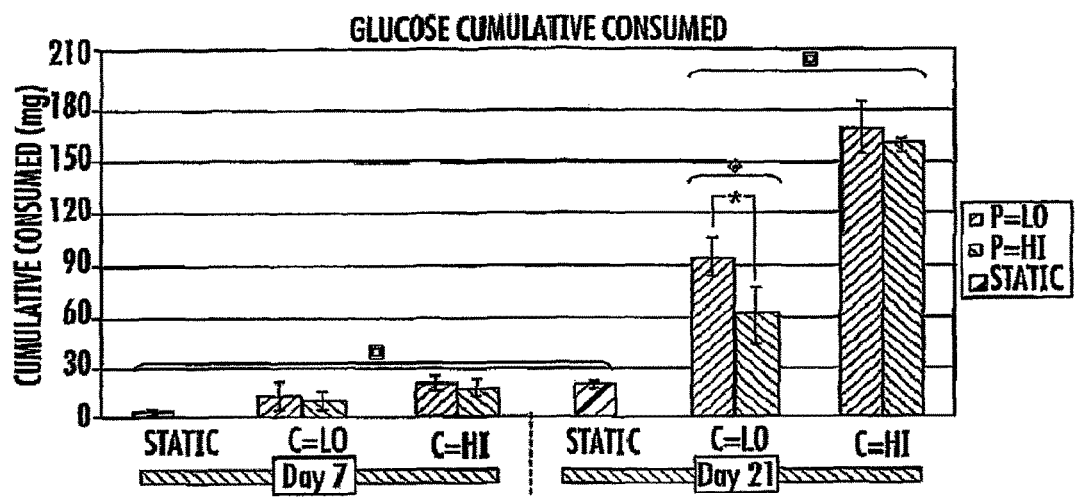
FIG. 11 illustrates cumulative glucose consumed in the bioreactor study described in Example 2.
Figure 12:
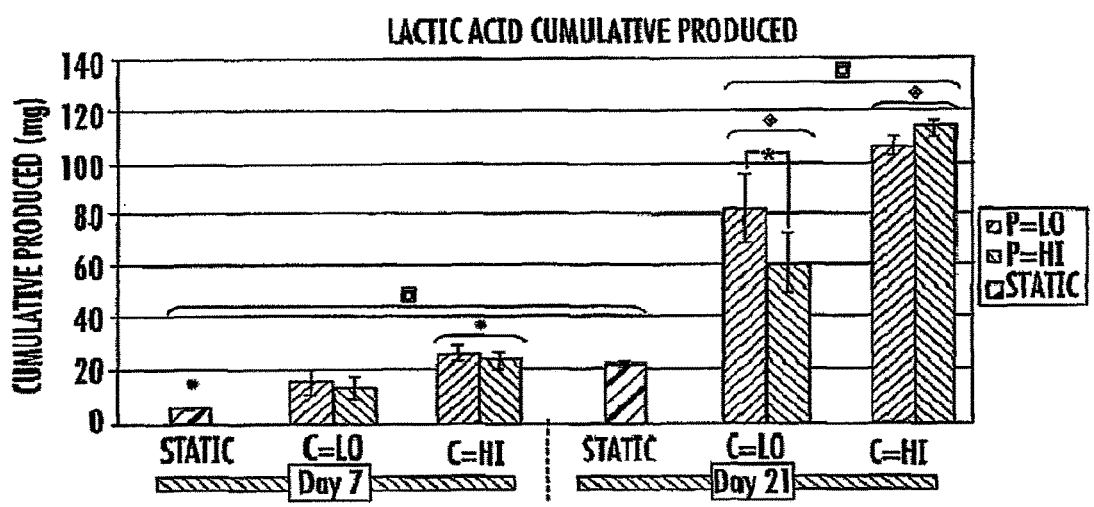
FIG. 12 illustrates cumulative lactic acid produced in the bioreactor study described in Example 2.
Figure 13:
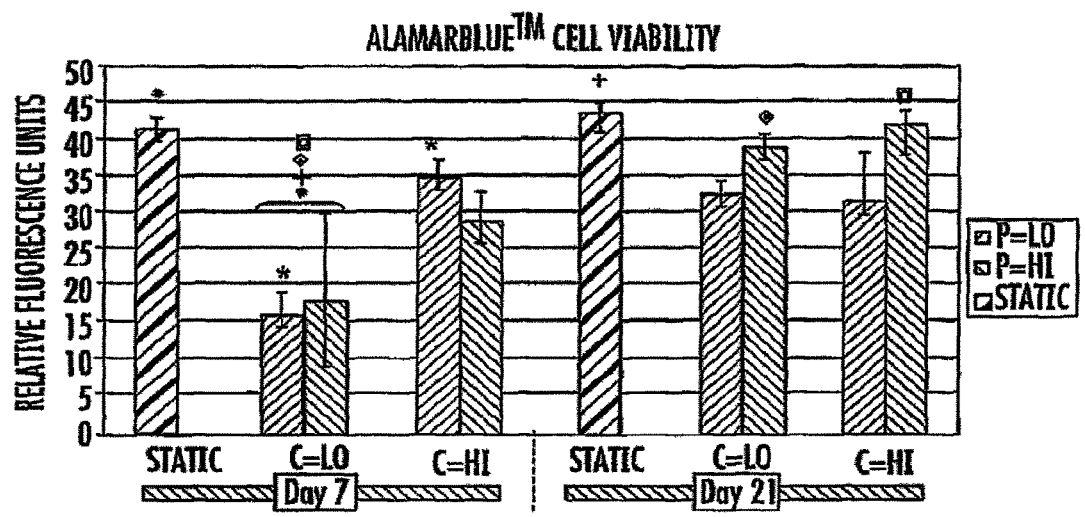
FIG. 13 illustrates AlamarBlue™ cell viability assay results in the bioreactor study described in Example 2.

The acellular control setup for study 1 presented no numerical elevation in lactic acid levels due to PLL hydrolysis (FIG. 6). Cumulative levels of glucose consumption and lactic acid production increased over the 21-day duration of studies 2 and 3 (FIG. 7). Live/dead imaging depicted a confluent cell layer at the PLL bead surface (not shown). Comparative cellular metabolic activity of the experimental and control systems of study 4 demonstrated similar numerical values for cumulative metabolic solutes and AlamarBlue™ relative fluorescence units (FIGS. 8-10).

As can be seen, the modular bioreactor provided an in vitro environment conducive for cell growth on three-dimensional scaffolds. Metabolic data demonstrated that cells continued to flourish over the duration of each preliminary study. Endpoint evaluations with AlamarBlue™ and live/dead fluorescent microscopy provided additional evidence as to the ongoing viability of cells cultured in the bioreactor system.

Example 2

Dynamic bioreactor systems were utilized to examine the influence of multiple mechanical stimuli on the differentiation traits of adult mesenchymal stem cells in addition to a variety of other cell types. The bioreactor was designed to model the in vivo conditions through available system conditions including hydrostatic loading. Perfusion of medium through the system was also adjusted to provide physiological levels of fluid shear stress across the cells.

Bioreactor systems such as that illustrated in FIG. 5 were prepared. Each 0.2 mL volume culture chamber was loaded with 45 mg PolyGraft™ granular material. A silicone diaphragm/gasket and four clamping socket screws were used to provide leak-free assembly of the culture chamber adjacent a pressure module.

All systems utilized a DI cell line grown in quantity using standard cell culture flasks (Corning). The initial cell culture medium consisted of DMEM (ATCC) supplemented with 10% FBS and 1% antibiotic/antimycotic. Each bioreactor flow circuit, including the culture chamber loaded with the granular scaffold, was primed and pre-wetted with medium prior to cell seeding. Each medium storage bottle was filled with 30 mM of the initial cell culture medium. Each bioreactor setup was seeded with a total of 6.0E5 cells by injecting one milliliter of the cell suspension directly into the flow circuit and culture chamber.

Five different treatment regimens were designed having different combinations of perfusion flow rate and hydrostatic compression characteristics. According to the regimens, perfusion flow was set to static, low or high. Low perfusion flow was set as 0.35 mL/min, and high perfusion flow was 0.70 mL/min. For those treatment regimens requiring only perfusion flow (i.e., no hydrostatic compression component), continuous perfusion of the bioreactor flow circuit occurred for the duration of the study with the exception of medium changes and aliquot sampling.

Hydrostatic compression was either low, at 0 kPa, or high, at 200 kPa. Treatment regimens applying both perfusion flow and hydrostatic compression underwent a daily schedule including 22 hours of continuous perfusion flow followed by two hours of cyclic hydrostatic compression. Within the two hour time period, cyclic hydrostatic compression was applied for 10 minute increments followed by a five minute session of perfusion flow to provide cells with fresh nutrients and remove damaging waste products. The experimental protocol of shifting from compression to perfusion and back to compression was repeated for the duration of the two hour period. Compression was applied at 200 kPa and cycled at 0.5 Hz (one second on and one second off). Specific treatment regiments were as shown below in Table 2.

TABLE 2

| Regimen Number | Perfusion (mL/min) | Compression (kPa) |
| --- | --- | --- |
| 1 | 0.35 | 0 |
| 12 | 0.70 | 0 |
| 3 | 0.35 | 200 |
| f4. | 0.70 | 200 |
| 5 | Static | Static |

The initial supplemented medium of DMEM, FBS and antibiotic/antimycotic was used through day 2. At day 2, the initial medium was modified with the following additional supplements to formulate an osteogenic differentiation medium: 50 µg/mL-ascorbic acid 2-phosphate, 3 mM 13-glycerophosphate, 10 nM Dexamethosone. Complete change of the supplemented medium took place on days 2, 8, 14 and 20.

Lactic acid production and glucose consumption were monitored throughout the course of the runs by taking medium samples every two or three days. Each treatment regimen was carried out in six bioreactor setups. Each regimen was assayed at day 7 and day 21 to provide a variety of quantitative, comparable data across all treatment combinations. Upon reaching a designated endpoint of either day 7 or 21, each of three of the setups were disassembled, and a variety of assay methodologies were carried out.

FIGS. 11-17 graphically illustrate the assay results obtained for determination of cumulative glucose consumed, cumulative lactic acid produced, AlamarBlue™ cell viability, total protein content, alkaline phosphatase activity, calcium content, and phosphorous content, respectively.

Visual observation of the cell-scaffold constructs upon removal from the culture chamber recognized that the constructs retained much of the bulk shape as packed in the culture chamber. Samples undergoing high hydrostatic compression appeared to maintain a tighter packing of the granular cluster following transfer from the culture chamber. The inclusion of mechanical stimuli in the experimental protocol clearly upregulated the cumulative metabolic requirements of cells when compared to static culture conditions. Hydrostatic compression also appeared to further increase the rate of glucose consumption and lactic acid production as can be seen with reference to FIG. 11 and FIG. 12. While the dynamic experimental conditions appeared to possess higher metabolic rates, the endpoint cell viability ascertained through the AlamarBlue™ assay conveyed a result of consistency regardless of whether dynamic or static conditions were applied, as can be seen with reference to FIG. 13.

Figure 14:
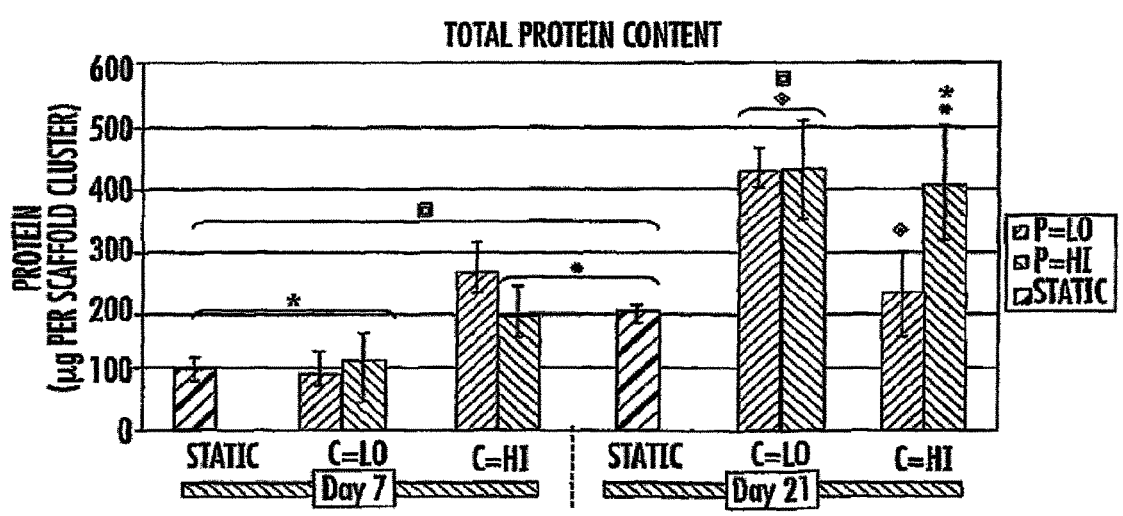
FIG. 14 illustrates total protein content assay results in the bioreactor study described in Example 2.

The dynamic mechanical stimulus of the culture chambers appeared to prompt extra-cellular matrix (ECM) production as indicated by the total protein content results (FIG. 14). The culture chamber design was intended to mimic in vivo conditions and in effect cause the cells to product bone-like ECM. Total protein content was clearly improved by day 21 as compared to the static culture protocol. As occurs in vivo, the active loading within the culture chamber can force a cell to lay down new ECM to surround itself with new "bone" and afford the cell's 30 long-term anchorage to the scaffold for continued survival.

Figure 15:
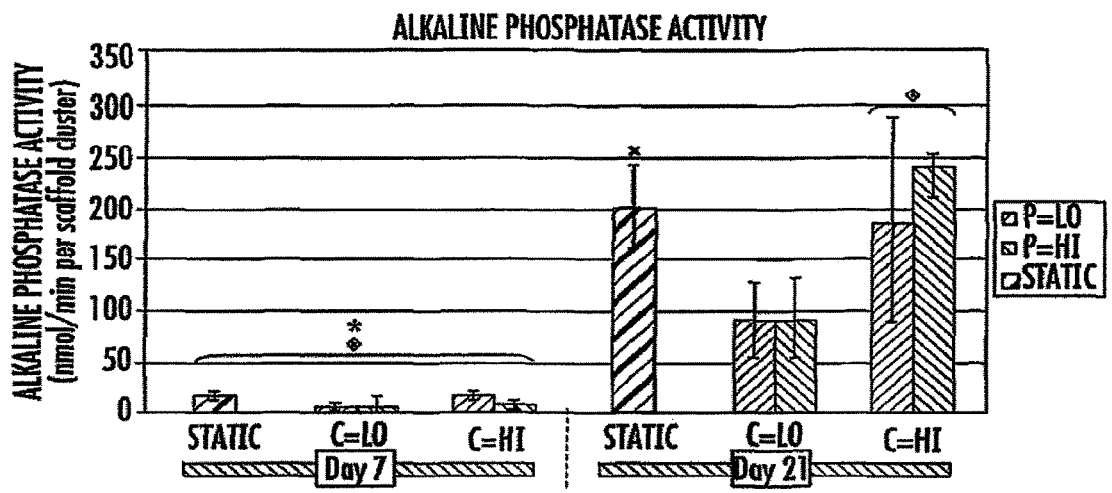
FIG. 15 illustrates alkaline phosphatase activity in the bioreactor study described in Example 2.
Figure 16:
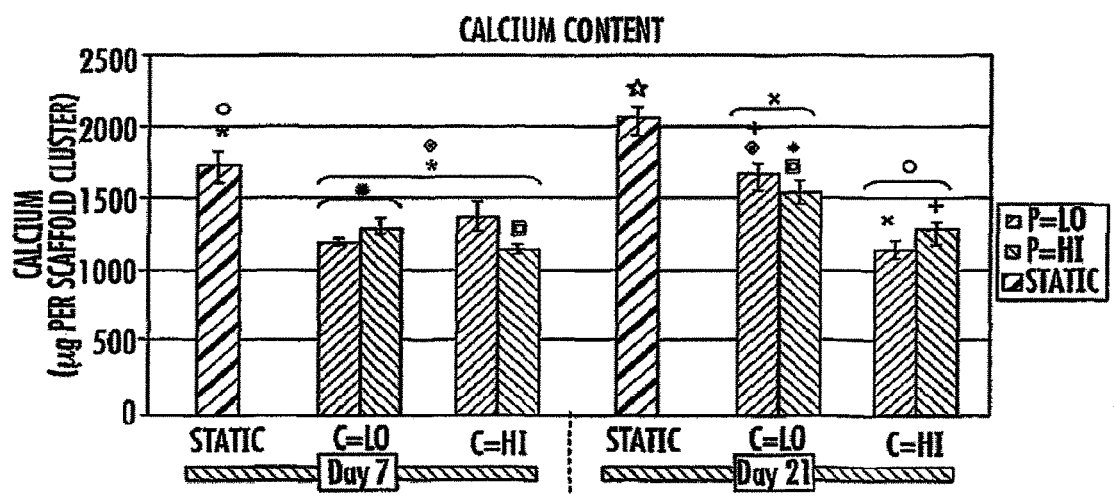
FIG. 16 illustrates calcium content assayed in the bioreactor study described in Example 2.
Figure 17:
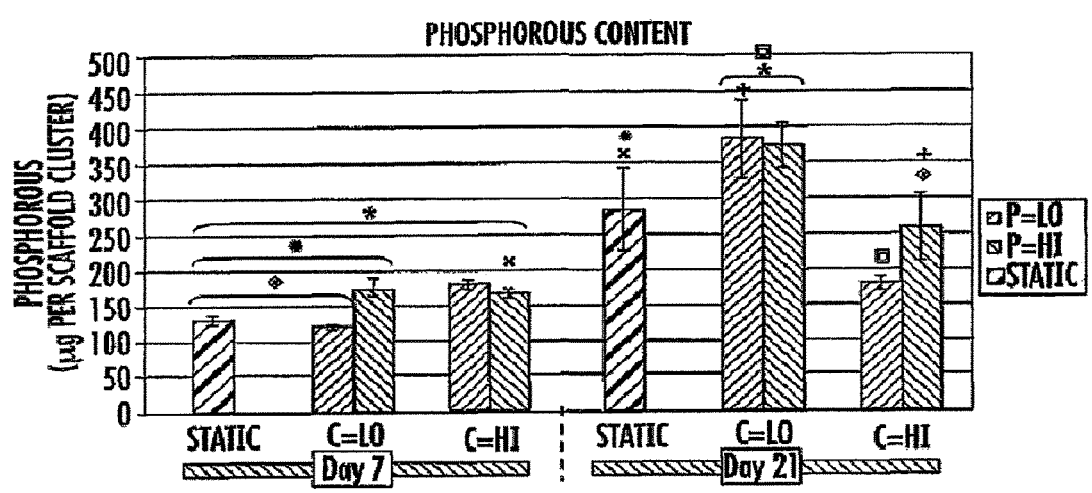
FIG. 17 illustrates phosphorous content assayed in the bioreactor study described in Example 2.

ALP activity has often been used to indicate cell differentiation toward the osteogenic lineage. In this case, both the static culture and high compression protocols indicated increased levels of cell differentiation through the statistical increase in ALP activity from day 7 to day 21 (FIG. 15).

Calcium and phosphorous contents (FIG. 16 and FIG. 17) appeared to uniquely vary over time as well as in respect to the static culture regimens. Studies that did not undergo hydrostatic compression demonstrated a statically significant increase in both calcium and phosphorous content from day 7 to day 21. Studies including hydrostatic compression showed no statistical change and even slight numerical reduction in calcium and phosphorous content over time. It is believed that the effect of compression may have broken up the more brittle mineralized portion of the ECM, allowing fragments to be swept out of the chamber by the ensuing perfusion flow, thereby reducing the endpoint level of calcium and phosphorous within the three dimensional construct.

These and other modifications and variations to the present disclosure can be practiced by those of ordinary skill in the art, without departing from the spirit and scope of the present disclosure, which is more particularly set forth in the appended claims. In addition, it should be understood that aspects of the various embodiments can be interchanged both, in whole, or in part. Furthermore, those of ordinary skill in the art will appreciate that the foregoing description is by way of example only and is not intended to limit the disclosure so further described in such appended claims.

Example 3

Novel 3D Cell Culture System

The use of injection-molded culture chambers (FIG. 18) allows the researcher to load the desired 3D scaffold material (FIG. 18, component A) of interest into two opposing culture chambers. The culture chambers can accommodate a variety of scaffold configurations including discrete beads, continuous porous constructs (e.g., sponge-like), and hydrogels, all retained by an integrated screen (FIG. 18, component B) molded directly into the fluid ports.

Cells can be loaded in the scaffold material prior to plasticware assembly or seeded post-assembly via manual syringe perfusion through the culture chamber and scaffold. The placement of a solid gasket (FIG. 18, component C) between the opposing culture chambers allows for two independent samples (n=2) within each plasticware assembly. Each chamber receives an independent perfusion (FIG. 18, component D) of culture medium that can accommodate unique chemical or mechanical stimulus for multiple experimental treatments. Integrated inlet and outlet ports are standard luer connectors that facilitate leak-free assembly within the perfusion fluid circuit. In one aspect, the 3D cell culture plasticware can facilitate advanced co-culture models by changing the solid gasket with a gasket-membrane assembly (FIG. 18, component E) to allow transfer of soluble factors and metabolites between different cell populations retained within the opposing chambers.

Peristaltic Assembly

Figure 19:
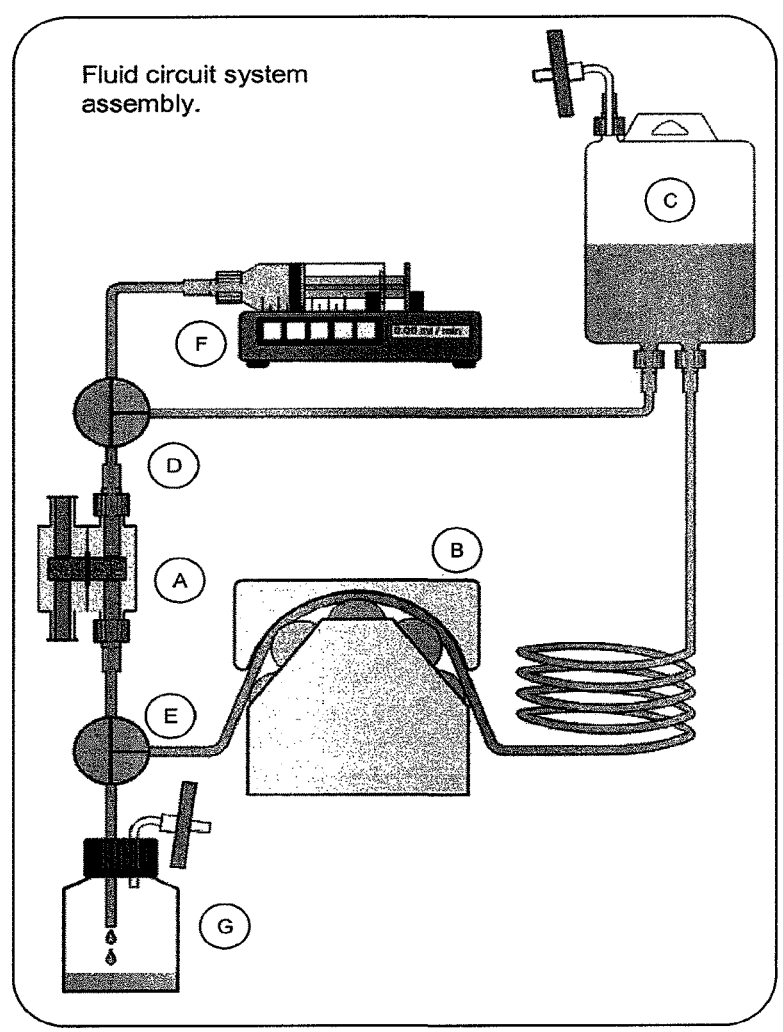
FIG. 19 shows components of fluid circuit system assembly.

The system assembly (FIG. 19) incorporates a two chamber bioreactor assembly (FIG. 19A) into a peristaltic-driven closed fluid circuit (FIG. 19, component B) with medium reservoir (FIG. 19, component C) to provide continuous perfusion into the culture chamber. Three-way valves (FIG. 19, components D, E) allow the system to switch to syringe pump-driven perfusion (FIG. 19, component F) for periodic delivery of growth hormone and collection (FIG. 19, component G) of soluble factors and metabolite products. A mirror image of the system setup is used to perfuse the independent sample in the second culture chamber (n=2).

In this example, the two chamber bioreactor assembly and the fluid circuit system assembly are used as described. 30 cell-scaffold constructs are maintained at 37° C. in a humidified incubator with 95%/5% air/$CO_2$. A base culture medium consisting of minimum essential Eagle medium supplemented with sodium bicarbonate (1500 mg/L), sodium pyruvate (1 mM), insulin (0.01 mg/mL) and 1% penicillin-streptomycin is used. Base culture medium is contained in the medium reservoir and cells are seeded in the desired scaffold material and packed within the culture chambers. An initial volume of base medium is held in the reservoir to maintain the 30 culture throughout the study duration. The 3D cell-scaffold constructs experience a perfusion flow rate throughout the study, with the exception of the syringe pump treatment regimens.

The 30 cell-scaffold constructs undergo periodic treatment with (+) or without (−) growth stimulant supplement (i.e., growth factor or growth hormone) to the culture medium. 2D culture would require manual supplementation of the base culture medium (+) or (−) growth stimulant followed by manual aspiration and replenishment of fresh base medium. In this 3D example, the cell-scaffold constructs undergo a more automated transition to the syringe pump perfusion of the treatment medium (+) or (−). The frequency of (+) or (−) treatment application can be established to occur multiple times daily for a variable length of time as prescribed by the experimental protocol.

An additional experimental factor can involve supplementing the base culture medium with pharmaceutical compounds and repeating the 30 culture protocols performed previously in combination with periodic treatment of (+) and (−) growth stimulant. Daily aliquots of the culture medium are collected to assess the metabolism of the pharmaceutical supplements. Analytical assessment of aliquots can include metabolite and protein screening.

The endpoint for a given study can involve rinsing the 3D cell culture with phosphate buffered saline. 3D cell-scaffold constructs are removed from the plasticware and placed in sterile tubes for cell isolation. Following centrifugation, supernatant is aspirated resulting in an isolated cell pellet. The cell pellet derived from the 3D culture can be snap frozen and stored at −80° C. Analytical assessment can include protein content, enzyme activity, qPCR, sequencing, etc.

Example 4

Dynamic 3D Co-Culture Vs. Static 2D

A comparison of 3D co-culture and 2D static systems was conducted on two oncogenic cell lines, the Human Liver cell line, HepG2 and MCF7 Human Breast Cancer Line. Both cell lines were obtained from the ATCC. Cell passage for the HepG2 cells was conducted 4 times in the 3D culture and 11 times in the 2D static system. Cells were plated at a concentration of $9.0 \times 10^5$ cells/chamber (3D) and $1.0 \times 10^5$ cells/chamber (2D). In the assays utilizing MCF7 cells, 3D passage was conducted 5 times with a plating of $3.3 \times 10^5$ cells/chamber. The 2D static culture of MCF7 cells was passaged 6 times and seeded at a concentration of $9.0 \times 10^4$ cells/chamber. For both cell types and culture systems, cells were grown in minimum essential eagle medium supplemented with Sodium bicarbonate 1500 mg/L, Sodium pyruvate 1 mM, FBS 10%, and Antibiotic 1%. A flow rate of 1 mL/min was used in all experiments. A 3D Scaffold of Alginate beads (cells encapsulated) with a scaffold diameter of ~1 mm was used to support the cell culture. 2D static cultures were conducted in 12-well plates with no scaffolds. Cells were assayed at 0, 2 and 6 days following culture. Albumin production was measured in the HepG2 cells, Cathepsin D activity in the MCF7 cells and Hoechst dye cell counts conducted with both cell types (see FIG. 21). 3D confocal laser microscopy was performed in situ via 3D plasticware imaging window. 3D cell populations demonstrated restrained growth curves while 2D culture grew in an exponential fashion. Numerical trends in cell function assays demonstrated good physiological response by cells in 3D culture while 2D cells were limited or trended down in their response. 3D confocal microscopy provided good images of cells stained with calcein and ethidium homodimer-1. Image depth was limited by the alginate bead scaffold material.

Example 5

HepG2 Human Liver Line obtained from the ATCC were passaged 14 times before being seeded in a cell chamber 10 at a concentration of $6.3 \times 10^5$ cells/chamber. Cells were grown in minimum essential eagle medium supplemented with Sodium bicarbonate 1500 mg/L, Sodium pyruvate 1 mM, FBS 10%, and Antibiotic 1%. A flow rate of 1 mL/min was used to move media through the inlet into the cell chamber and out through the outlet. A 3D Scaffold of Alginate beads (cells encapsulated) with a scaffold diameter of ~1 mm was used to support the cell culture. Cells were assayed at 0, 2 and 6 days following culture. The assays conducted on the cells included Hoechst dye cell count, AlamarBlue cell metabolism, and 3D confocal laser microscopy in situ (see FIG. 22). Hoechst cell count and alamarBlue cell metabolism assays demonstrated excellent correlation of the averages (0.995) in assessing the 3D cell populations at various timepoints. DiIC12(3) fluorescent dye also proved useful for longer duration staining and imaging of live cells under 30 confocal microscopy.

What is claimed is:

1. A method of assessing cell survival, cell proliferation and/or cell attachment characteristics in cell samples, comprising:

introducing a cell sample into a first cell culture chamber of a first cell module of a bioreactor system, the first cell module defining the cell culture chamber, an inlet, an outlet, and a port opening, and further comprising a least one male fitting comprising an indentation and at least one female fitting comprising a raised portion, wherein the male and female fitting are located on a same face of the first cell module;

introducing a cell culture medium that encourages migration into a second cell culture chamber of a second cell module, wherein the second cell module is identical to the first cell module, and wherein a permeable or semi-permeable membrane is sealingly engaged between the port openings of the first and second cell module by alignment of the male and female fittings of the first cell module with the corresponding male and female fittings of the second cell module; and assessing cell survival, cell proliferation, and/or cell attachment based on detecting migration of one or more cells from the first cell module to the second cell module via the permeable or semi-permeable membrane.

2. The method of claim 1, wherein the one or more cells are obtained from a biopsy of a subject.

3. The method of claim 1, wherein the cell culture medium in the second chamber comprises a higher concentration of serum, cytokines, chemokines, or combination thereof.

4. The method of claim 1, wherein one or more of electric current, pressure, and media flow rate are employed to modify migration of the cell sample into the second chamber.

5. The method of claim 1, further comprising separating or isolating migratory cells from non-migratory cells after migration is induced by isolating migratory cells from the second chamber or non-migratory cells from the first chamber.

6. The method of claim 5, wherein the separating or isolating comprises detecting the presence or absence of a marker or indicator, wherein the presence or absence of the marker or indicator indicates a desired cell type.

7. The method of claim 6, wherein the desired cell type is a stem cell, and wherein the stem cell is from a mixed population of cells.

8. The method of claim 7, wherein the mixed population of cells comprises bone marrow cells or umbilical cord blood cells.

9. The method of claim 5, wherein the method allows identification of a disease involving excessive or insufficient angiogenesis.

10. The method of claim 9, wherein the disease involving excessive angiogenesis is selected from the group consisting of rheumatoid arthritis, cancer, psoriasis, and diabetic retinopathy.

11. The method of claim 9, wherein the disease involving insufficient angiogenesis is selected from the group consisting of stroke, heart disease, ulcers, infertility, and scleroderma.

12. The method of claim 1, further comprising screening one or more agents that inhibit or promote cell migration by passing an agent through the inlet and outlet of the first cell module, second cell module, or both, wherein an increase in cell migration from the first cell module to the second cell module indicates that the one or more agents promote cell migration and a decrease in cell migration indicates that the one or more agents inhibit cell migration.

13. The method of claim 12, wherein inhibition or promotion of cell migration indicates inhibition or promotion of cell invasion, wound healing, metastasis, vasculogenesis, immune responses, angiogenesis, tumor formation, and chemotaxis.

14. The method of claim 1, wherein the membrane has a pore size between 0.2 μl and 10 μl.

15. The method of claim 1, wherein the one or more cells are cancer cells, wherein the cancer is selected from the group consisting of lymphoma, B cell lymphoma, T cell lymphoma, mycosis fungoides, Hodgkin's Disease, myeloid leukemia, bladder cancer, brain cancer, nervous system cancer, head and neck cancer, squamous cell carcinoma of head and neck, kidney cancer, lung cancers, such as small cell lung cancer and non-small cell lung cancer, neuroblastoma/glioblastoma, ovarian cancer, pancreatic cancer, prostate cancer, skin cancer, liver cancer, melanoma, squamous cell carcinomas of the mouth, throat, larynx, and lung, colon cancer, cervical cancer, cervical carcinoma, breast cancer, and epithelial cancer, renal cancer, genitourinary cancer, pulmonary cancer, esophageal carcinoma, head and neck carcinoma, large bowel cancer, hematopoietic cancers, testicular cancer, colon and rectal cancers, prostate cancer, and pancreatic cancer.

16. A method of assessing biochemical communication between different cell types and the influence of said communication on the growth and development of cells, comprising:
   introducing a cell sample into a first cell culture chamber of a first cell module of a bioreactor system, the first cell module defining the cell culture chamber, an inlet, an outlet, and a port opening, and further comprising a least one male fitting comprising an indentation and at least one female fitting comprising a raised portion, wherein the male and female fitting are located on a same face of the first cell module;
   introducing a cell culture medium or a second cell sample in a second cell culture chamber of a second cell module, wherein the second cell module is identical to the first cell module, and wherein a permeable or semi-permeable membrane is sealingly engaged between the port openings of the first and second cell module by alignment of the male and female fittings of the first module with the corresponding male and female fittings of the second cell module; and
   assessing biochemical communication between different cell types based on regulating the local environment within the first and second chambers and detecting growth and development of one or more cells in the first or second cell module.

17. The method of claim 16, wherein each culture chamber of the bioreactor system is independently controlled while maintaining biochemical communication between the chambers.

18. A method of evaluating a triggering mechanism involved in cell differentiation, comprising:
   introducing a cell sample into a first cell culture chamber of a first cell module of a bioreactor system, the first cell module defining the cell culture chamber, an inlet, an outlet, and a port opening, and further comprising a least one male fitting comprising an indentation and at least one female fitting comprising a raised portion, wherein the male and female fitting are located on a same face of the first cell module;
   introducing a cell culture medium or second cell sample in a second cell culture chamber of a second cell module, wherein the second cell module is identical to the first cell module, and wherein a permeable or semi-permeable membrane is sealingly engaged between the port openings of the first and second cell module by alignment of the male and female fittings of the first cell module with the corresponding male and female fittings of the second cell module; and
   assessing cell differentiation based on regulating the biological communication between the first and second chambers and detecting migration of one or more cells from the first cell module to the second cell module via the permeable or semi-permeable membrane.

19. The method of claim 18, wherein the cell sample is undifferentiated stem cells.

20. The method of claim 18, wherein the cell culture medium comprises one or more types of feeder cells.

21. The method of claim 18, wherein the cell differentiation is stem cell differentiation.

22. The method of claim 18, further comprising identifying and isolating a desired cell type from the population of cells.

23. The method of claim 18, wherein the method provides isolated, differentiated cells for implantation into a subject.

* * * * *

UNITED STATES PATENT AND TRADEMARK OFFICE
CERTIFICATE OF CORRECTION

PATENT NO. : 10,466,232 B2  
APPLICATION NO. : 15/406396  
DATED : November 5, 2019  
INVENTOR(S) : Matthew R. Gevaert and David E. Orr Page 1 of 3

It is certified that error appears in the above-identified patent and that said Letters Patent is hereby corrected as shown below:

In the Drawings

Sheet 7, FIG. 6, y-axis label, replace "CONCETRATION" with --CONCENTRATION--.
Sheet 12, FIG. 17, title, replace "PHOSPHOROUS" with --PHOSPHORUS--.
Sheet 12, FIG. 17, y-axis label, replace "PHOSPHOROUS" with --PHOSPHORUS--.

In the Specification

Column 4, Line 20, replace "phosphorous" with --phosphorus--.
Column 4, Line 22, replace "30" with --3D--.
Column 4, Line 31, replace "culture;" with --culture.--.
Column 8, Line 63, replace "primary-rat" with --Primary-rat--.
Column 8, Line 65, replace "NIH 3T3" with --NIH/3T3--.
Column 9, Lines 3-4, replace "Primary-ratAortaSMC" with --Primary-rat Aorta SMC--.
Column 9, Line 14, replace "AortaEC" with --Aorta EC--.
Column 9, Line 16, replace "BladderSMC" with --Bladder SMC--.
Column 9, Line 23, replace "Intersticial" with --Interstitial--.
Column 9, Line 26, replace "Vase" with --Vasc--.
Column 9, Line 34, replace "Primary-Vase" with --Primary-Vasc--.
Column 9, Line 40, replace "Cl 7.2" with --C17.2--.
Column 9, Line 43, replace "Primary h" with --Primary-h--.
Column 9, Line 52, replace "Stertoli" with --Sertoli--.
Column 9, Line 55, replace "Primary-Vase" with --Primary-Vasc--.
Column 9, Line 57, replace "Glioblast" with --Glioblastoma--.
Column 9, Line 61, replace "HVIintersticial" with --HV Interstitial--.
Column 9, Line 63, replace "CorneaFB" with --Cornea FB--.
Column 9, Line 64, replace "ral" with --Oral--.
Column 10, Line 4, replace "Vase" with --Vasc--.
Column 10, Line 6, replace "VascularEC" with --Vascular EC--.
Column 10, Line 12, replace "Vase" with --Vasc--.

Signed and Sealed this  
Third Day of November, 2020

Andrei Iancu  
*Director of the United States Patent and Trademark Office*

CERTIFICATE OF CORRECTION (continued)
U.S. Pat. No. 10,466,232 B2

Column 10, Line 13, replace "BI6.FI0" with --B16-F10--.
Column 10, Line 14, replace "3HIOTI/2" with --3H10T1/2--.
Column 10, Line 24, replace "Primary-h·Lymph" with --Primary-h Lymph--.
Column 10, Line 25, replace "TCell" with --T Cell--.
Column 10, Line 35, replace "MeniscusC" with --Meniscus C--.
Column 10, Line 52, replace "Vase" with --Vasc--.
Column 10, Line 52, replace "Vase" with --Vasc--.
Column 10, Line 54, replace "HEC-IB" with --HEC-1B--.
Column 10, Line 54, replace "U1 78" with --U178--.
Column 10, Line 61, replace "DOV 13" with --DOV13--.
Column 10, Line 62, replace "CorneaFB" with --Cornea FB--.
Column 11, Line 3, replace "Primary-Vase" with --Primary-Vasc--.
Column 11, Line 6, replace "Ebryo" with --Embryo--.
Column 11, Line 12, replace "PE-·0041" with --PE-0041--.
Column 11, Line 17, replace "Vase" with --Vasc--.
Column 11, Line 26, replace "Arachnoidal" with --Arachnoid--.
Column 11, Line 33, replace "RTl 12" with --RT112--.
Column 11, Line 36, replace "Par-ClO" with --Par-C10--.
Column 11, Line 44, replace "AlO" with --A10--.
Column 11, Line 46, replace "Salisphere" with --Sanisphere--.
Column 11, Line 63, replace "Perosteum" with --Periosteum--.
Column 11, Line 66, replace "Pane 1" with --Panc 1--.
Column 12, Line 6, replace "TCell" with --T Cell--.
Column 12, Line 7, replace "primary-rabbit" with --Primary-rabbit--.
Column 12, Line 13, replace "HCT-8/El1" with --HCT-8/E11--.
Column 12, Line 19, replace "C5.1 8" with --C5.18--.
Column 12, Line 21, replace "HEKOO1" with --HEK001--.
Column 12, Line 35, replace "Vase" with --Vasc--.
Column 12, Line 36, replace "Salisphere" with --Sanisphere--.
Column 12, Line 42, replace "Tcell" with --T cell--.
Column 12, Line 48, replace "Vase" with --Vasc--.
Column 12, Line 49, replace "Vase" with --Vasc--.
Column 12, Line 65, replace "Pancreasislets" with --Pancreas Islets--.
Column 15, Line 2, replace "height" with --height.--.
Column 16, Line 55, replace "polyphophazenes" with --polyphosphazenes--.
Column 17, Line 38, replace "utethane" with --urethane--.
Column 17, Lines 40-41, replace "PEI polyethylene" with --PE/polyethylene--.
Column 17, Line 45, replace "Polyhydroxyalk: anoate" with --Polyhydroxyalkanoate--.
Column 17, Line 61, replace "Te(C0)(5)/" with --Fe(CO)(5)/--.
Column 17, Line 63, replace "Dextran·(modified" with --Dextran (modified--.
Column 18, Line 1, replace "glutaminate" with --glutamate--.
Column 18, Lines 1-2, replace "HEA ihydroxyethyl" with --HEA/hydroxyethyl--.
Column 18, Line 4, replace "hydorxyanisole" with --hydroxyanisole--.
Column 18, Line 9, replace "Organo Clay" with --Organoclay--.
Column 18, Line 12, replace "omithine" with --ornithine--.
Column 18, Line 17, replace "polyethyle-neoxide" with --polyethylene oxide--.

CERTIFICATE OF CORRECTION (continued)
U.S. Pat. No. 10,466,232 B2

Column 18, Line 22, replace "acrylamidomethylpropanesulfonicsodiu" with --acrylamidomethylpropanesulfonicsodium--.
Column 18, Line 26, replace "OPF/oligo [poly(ethylene glycol) fumarate]" with --OPF/oligo[poly(ethylene glycol) fumarate]--.
Column 19, Line 17, replace "fu" with --In--.
Column 20, Line 12, replace "non-, porous" with --non-porous--.
Column 20, Line 53, replace "Whatmann, and Sartorious" with --Whatman, and Sartorius--.
Column 25, Line 40, replace "mi" with --ml--.
Column 26, Line 6, replace "L glutamine" with --L-glutamine--.
Column 26, Line 7, replace "(Fisher):" with --(Fisher).--.
Column 26, Line 30, replace "DI" with --D1--.
Column 27, Line 59, replace "DI" with --D1--.
Column 28, Line 26, replace "regiments" with --regimens--.
Column 28, Line 33, replace "I2" with --2--.
Column 28, Line 35, replace "f4" with --4--.
Column 28, Line 43, replace "Dexamethosone" with --Dexamethasone--.
Column 28, Line 59, replace "phosphorous" with --phosphorus--.
Column 29, Line 20, replace "30" with --3D--.
Column 29, Line 27, replace "phosphorous" with --phosphorus--.
Column 29, Line 31, replace "phosphorous" with --phosphorus--.
Column 29, Line 34, replace "phosphorous" with --phosphorus--.
Column 29, Line 39, replace "phosphorous" with --phosphorus--.
Column 30, Line 27, replace "30" with --3D--.
Column 30, Line 38, replace "30" with --3D--.
Column 30, Line 42, replace "30" with --3D--.
Column 30, Line 56, replace "30" with --3D--.
Column 31, Line 62, replace "30" with --3D--.

In the Claims

Claim 1, Column 32, Line 4, replace "comprising a" with --comprising at--.
Claim 16, Column 33, Line 32, replace "comprising a" with --comprising at--.
Claim 18, Column 34, Line 15, replace "comprising a" with --comprising at--.